(12) United States Patent
Kawai et al.

(10) Patent No.: US 7,767,158 B2
(45) Date of Patent: Aug. 3, 2010

(54) SURFACE LIGHT-EMITTING DEVICE, FILTERING DEVICE USING SAME, AND OPTICALLY ASSISTED CERAMIC FILTER

(75) Inventors: Chihiro Kawai, Itami (JP); Ryuichi Inoue, Itami (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 907 days.

(21) Appl. No.: 11/628,947

(22) PCT Filed: May 27, 2005

(86) PCT No.: PCT/JP2005/009790

§ 371 (c)(1),
(2), (4) Date: Dec. 8, 2006

(87) PCT Pub. No.: WO2005/123246

PCT Pub. Date: Dec. 29, 2005

(65) Prior Publication Data

US 2008/0274018 A1      Nov. 6, 2008

(30) Foreign Application Priority Data

Jun. 15, 2004   (JP) .............................. 2004-176881
Dec. 6, 2004    (JP) .............................. 2004-352306

(51) Int. Cl.
*A61L 9/18*   (2006.01)
*A61L 9/20*   (2006.01)

(52) U.S. Cl. ....................................................... 422/121
(58) Field of Classification Search ..................... None
See application file for complete search history.

(56) References Cited

U.S. PATENT DOCUMENTS 7,468,529 B2 * 12/2008 Kawai et al. ................ 257/102
2005/0042743 A1   2/2005 Kawai et al.

FOREIGN PATENT DOCUMENTS

| JP | 2003-200043 | 7/2003 |
| JP | 2004-24461 | 1/2004 |
| WO | WO-2004/006969 | 1/2004 |

\* cited by examiner

*Primary Examiner*—Elizabeth L McKane
(74) *Attorney, Agent, or Firm*—Global IP Counselors, LLP

(57) ABSTRACT

A surface light-emitting device having a surface emitter for emitting visible light or ultraviolet light by electroluminescence also has multiple through-holes that define fluid channels for fluid flow in a direction orthogonal to the surface of the surface emitter. The present invention also provides an optically assisted ceramic filter composed of a ceramic filter having multiple channels, and a photocatalytic layer and surface emitter disposed on a side surface of the ceramic filter.

28 Claims, 7 Drawing Sheets

(a)

(b)

SURFACE LIGHT-EMITTING DEVICE, FILTERING DEVICE USING SAME, AND OPTICALLY ASSISTED CERAMIC FILTER

FIELD OF THE INVENTION

The present invention relates to a surface light-emitting device based on the use of a surface emitter having a function whereby visible light or ultraviolet light is emitted, a photocatalyst is excited, and hazardous substances are decomposed or sterilized; to a filtering device obtained using this device; and to an optically assisted ceramic filter.

BACKGROUND OF THE INVENTION

In conventional air purifiers and other such organic decomposition apparatuses that use photocatalysts, a porous substance supporting $TiO_2$ or another photocatalytic material is irradiated with ultraviolet light emitted from a mercury lamp or the like, and the photocatalyst is excited. However, the mercury lamp must be placed separately from the substance. Therefore, the entire apparatus becomes large when, for example, an air purifier is involved.

A method for exciting the photocatalyst by using a surface emitter as a light source has been proposed (see Japanese Laid-Open Patent Application No. 2003-200043). In this method, an organic EL light-emitting sheet that emits ultraviolet light or visible light having a short wavelength is used as a light source to excite the photocatalyst. For example, two sheets are stacked, and the hazardous components in the fluid between the two sheets are decomposed and eliminated by photocatalytic action. However, in order to treat a large quantity of fluid with this structure, the number of sheet layers must be increased and numerous channels must be created, and the apparatus itself becomes extremely large.

Demand has recently increased for ceramic filters having high heat resistance, high strength, and high permeability. Such ceramic filters are used in the food and chemical industries. Organic films have been used in these industries in the past, but ceramics have excellent heat resistance, pressure resistance, chemical resistance, and high functionality not found in organic films, and ceramics have been replacing organic films. Furthermore, ceramic filters are used as catalyst carriers, microbial culture carriers, and other such bioreactors and the like.

Commonly used ceramic filters have a cross section shaped as a lotus root, wherein multiple channels are formed perpendicular to a cross section, and filtration layers are formed on the inner walls of the channels. Permeability performance is improved in actual practice by reducing the thickness of the narrow-pore filtration layer portions necessary for filtration. Specifically, the structure is composed of filtration layers for performing filtration, and support members for supporting the filtration layers. Ceramic filters whose cross sections are about 30 mm in diameter and about 500 to 1000 mm in length are often used. Overall, the porosity is about 35 to 40%, the pore diameters of the filtration layers are about 0.005 to 1 μm, and the pore diameters of the intermediate layers and support members are about 2 to 3 μm and 10 to 20 μm, respectively. The total thickness of a filtration layer and an intermediate layer is about 100 to 200 μm. A feed solution is poured into the channels and filtered by the filtration layers, and the clarified liquid passes through the intermediate layers and the support members and is ejected from the side of the ceramic filter.

However, this type of ceramic filter is not capable of physical filtration based on the relationship between the pore diameter and the size of the collected substances.

In contrast to this method, a ceramic filter has been invented that functions so that a light emitter and electrodes themselves are fashioned into a porous structure, the porous structure itself emits ultraviolet light when fluid passes through the structure, and the photocatalyst supported in the porous structure decomposes organic matter or destroys bacteria and viruses (see International Application Publication Pamphlet No. 04/006969). The light emitter is obtained by sintering some semiconductor particles to a certain degree.

However, the following problems are encountered with this method.

(1) An advanced technique is needed to control the pore diameter and porosity of the porous light-emitting layer. Particularly, in the case of an air purifier or the like which requires high permeability, the pore diameter and porosity must be increased and large semiconductor particles must be used, but sintering declines when the particle diameter is increased. Also, a light-emitting layer having a high porosity is difficult to obtain by a powder-sintering method.

(2) Costs are higher because an electrode must be formed on the surface of the porous structure by sputtering or vapor deposition.

(3) When a liquid, particularly a highly conductive liquid, passes through the interior of the porous light-emitting layer, an electric field sometimes cannot be effectively applied if the electrode and the particles constituting the porous light-emitting layer are not completely insulated, and an advanced technique is required for this insulation process. In particular, an even more advanced technique is required and costs are incurred when the constituent particles are reduced in size.

SUMMARY OF THE INVENTION

Problems the Invention is Intended to Solve

An object of the present invention is to provide a surface light-emitting device in which a catalytic reaction can be efficiently performed without the use of an ultraviolet lamp, an ultraviolet LED, or another such external ultraviolet light source, and in which the catalytic reaction can be efficiently performed even in the case of a highly UV-absorbing contaminated fluid that cannot be treated with an external light source. Another object is to provide a surface light-emitting device that does not require advanced techniques and that can be obtained at low cost, wherein the light-emitting layer can be easily insulated.

Another object is to provide a ceramic filter that can be easily manufactured at low cost, and that has a function for decomposing organic matter or destroying bacteria and viruses.

Means for Solving these Problems

The inventors have designed a surface light-emitting device and a ceramic filter having unique structures as a method for resolving these problems. Specifically, the present invention comprises aspects (1) through (31).

(1) A surface light-emitting device comprising a surface emitter which has a function for emitting visible light or ultraviolet light by electroluminescence; and a plurality of through-holes defining channels for fluid flow in a direction orthogonal to the surface of the surface emitter.

(2) The surface light-emitting device according to (1), characterized in that a porous layer having a photocatalyst is disposed on the top and/or bottom surfaces of the surface emitter.

(3) The surface light-emitting device according to (1) or (2), characterized in that the channels are filled with a porous structure having a photocatalyst.

(4) The surface light-emitting device according to any of (1) through (3), characterized in that except for electrode portions, the surface emitter is electrically insulated from the exterior.

(5) The surface light-emitting device according to any of (1) through (4), characterized in that the surface emitter has a plurality of rectangular light-emitting layers placed at fixed gap intervals, wherein the gaps constitute the channels.

(6) The surface light-emitting device according to any of (1) through (4), characterized in that the surface emitter has light-emitting layers placed in a lattice formation, wherein the gaps constitute the channels.

(7) The surface light-emitting device according to any of (1) through (6), wherein the emitted visible light or ultraviolet light is concentrated in the channels.

(8) The surface light-emitting device according to (7), wherein the light-emitting layers of the surface emitter are enclosed by members that reflect visible light and/or ultraviolet light.

(9) The surface light-emitting device according to any of (1) through (8), characterized in that the surface area occupied by the channels (channel surface area ratio) is 30 to 70% of the entire surface of the surface emitter.

(10) The surface light-emitting device according to any of (1) through (9), characterized in that the peak wavelength of the spectrum of light emitted by the surface emitter is 540 nm or less.

(11) The surface light-emitting device according to (10), characterized in that the peak wavelength of the spectrum of light emitted by the surface emitter is 460 nm or less.

(12) The surface light-emitting device according to (11), characterized in that the peak wavelength of the spectrum of light emitted by the surface emitter is 400 nm or less.

(13) The surface emitter according to any of (1) through (12), characterized in that an inorganic EL device or an organic EL device is used as the surface emitter.

(14) The surface emitter according to (13), characterized in that the general formula for the phosphor used in the inorganic EL device is $Zn_{(1-x)}A_xS:Cu,D$ (wherein A is at least one type of 2A group element selected from among Be, Mg, Ca, Sr, and Ba; D is at least one type of element selected from among 3B group elements or 7B group elements; and the value of x is $0<x<1$), and the phosphor has a function for emitting Blue-Cu light.

(15) The surface emitter according to (13), characterized in that the general formula for the phosphor used in the inorganic EL device is $Zn_{(1-x)}A_xS:Ag,D$ (wherein A is at least one type of 2A group element selected from among Be, Mg, Ca, Sr, and Ba; D is at least one type of element selected from among 3B group elements or 7B group elements; and the value of x is $0<x<1$), and the phosphor has a function for emitting Blue-Cu light.

(16) The surface light-emitting device according to any of (2) through (15), characterized in that the porous layers having a photocatalyst are a foamed metal, a foamed ceramic, or a woven resin fabric.

(17) The surface light-emitting device according to any of (2) through (16), wherein the porous layers having a photocatalyst are ceramic filters.

(18) The surface light-emitting device according to (17), characterized in that the ceramic filters have a plurality of channels, and the channels are communicated with the channels of the surface light-emitting device.

(19) The surface light-emitting device according to any of (2) through (18), characterized in that the porous layers and porous structure having a photocatalyst have an average pore diameter of 500 μm or less.

(20) The surface light-emitting device according to any of (2) through (19), characterized in that the surface emitter and the porous layers are repeatedly stacked.

(21) A filtering device obtained using the surface light-emitting device according to any of (1) through (20).

(22) A filter for an air purifier or an air conditioner obtained using the filtering device according to (21).

(23) An optically assisted ceramic filter, characterized in comprising a ceramic filter having a plurality of channels, and a photocatalytic layer and a surface emitter disposed on a side surface of the ceramic filter.

(24) The optically assisted ceramic filter according to (23), characterized in that the channels of the ceramic filter are orthogonal to a cross section of the ceramic filter.

(25) The optically assisted ceramic filter according to (23) or (24), characterized in that a plurality of through-holes are formed in the surface emitter in a direction orthogonal to the surface of the surface emitter.

(26) The optically assisted ceramic filter according to any of (23) through (25), characterized in that the peak wavelength of the spectrum of light emitted by the surface emitter is 460 nm or less.

(27) The optically assisted ceramic filter according to any of (26), characterized in that the peak wavelength of the spectrum of light emitted by the surface emitter is 400 nm or less.

(28) The optically assisted ceramic filter according to any of (23) through (27), characterized in that the surface emitter emits light by dispersive inorganic EL.

(29) The optically assisted ceramic filter according to (28), characterized in that the inorganic EL electrodes are formed from a light-reflecting material.

(30) The optically assisted ceramic filter according to (28) or (29), characterized in that the general formula for the phosphor used in the inorganic EL device is $Zn_{(1-x)}A_xS:Cu,D$ (wherein A is at least one type of 2A group element selected from among Be, Mg, Ca, Sr, and Ba; D is at least one type of element selected from among 3B group elements or 7B group elements; and the value of x is $0<x<1$), and the phosphor has a function for emitting Blue-Cu light.

(31) The optically assisted ceramic filter according to (28) or (29), characterized in that the general formula for the phosphor used in the inorganic EL device is $Zn_{(1-x)}A_xS:Ag,D$ (wherein A is at least one type of 2A group element selected from among Be, Mg, Ca, Sr, and Ba; D is at least one type of element selected from among 3B group elements or 7B group elements; and the value of x is $0<x<1$), and the phosphor has a function for emitting Blue-Cu light.

EFFECTS OF THE INVENTION

In the surface light-emitting device of the present invention, a photocatalyst can be excited by a surface emitter that emits visible light or ultraviolet light. The surface light-emitting device of the present invention is placed and operated in a contaminated fluid, whereby a catalytic reaction can be efficiently performed without the use of an ultraviolet lamp, an ultraviolet LED, or another such external ultraviolet light source. In particular, a catalytic reaction can be efficiently performed in the case of a highly UV-absorbing contaminated fluid that cannot be treated with an external light source.

In the surface light-emitting device of the present invention, fluid does not pass through the light-emitting layer because multiple through-holes as channels for the fluid are formed in the surface emitter, and the light-emitting layer can be insulated without incurring extra costs.

A catalytic reaction vessel obtained using the surface light-emitting device of the present invention is capable of decomposing organic matter or destroying bacteria and the like, and can therefore be applied to various fields, including the decomposition and removal of contaminants in the atmosphere, such as NOx, SOx, CO gas, diesel particulates, pollen, dust, and ticks; the decomposition and removal of organic compounds contained in sewage; light sources for destroying common bacteria and viruses; the decomposition of harmful gases produced by chemical plants; the decomposition of odorous components; and sterilizing light sources in ultra-pure manufacturing apparatuses. Such a reaction vessel can also be applied to honeycomb structures for treating automobile exhaust, filters for air purifiers or air conditioners, sewage filters, various types of water purifiers, sterilization of spas, and insect repellents.

Using the optically assisted ceramic filter of the present invention makes regular filtration possible depending on physical size, and also allows smaller organic matter and bacteria/viruses that could not be collected by filtration to be decomposed by the photocatalytic function. The optically assisted ceramic filter of the present invention can also be easily manufactured at low cost.

DETAILED DESCRIPTION OF THE INVENTION

One essential structure of the surface light-emitting device of the present invention has a surface emitter having a function for emitting visible light or ultraviolet light, and a porous layer having a photocatalyst formed on the top surface and/or the bottom surface, wherein multiple through-holes define channels for fluid flow are formed in a direction perpendicular to the surface of the surface emitter. A light-emitting sheet known as an electroluminescence (EL) sheet is preferably used as the surface emitter having a function for emitting visible light or ultraviolet light.

Figure 1:
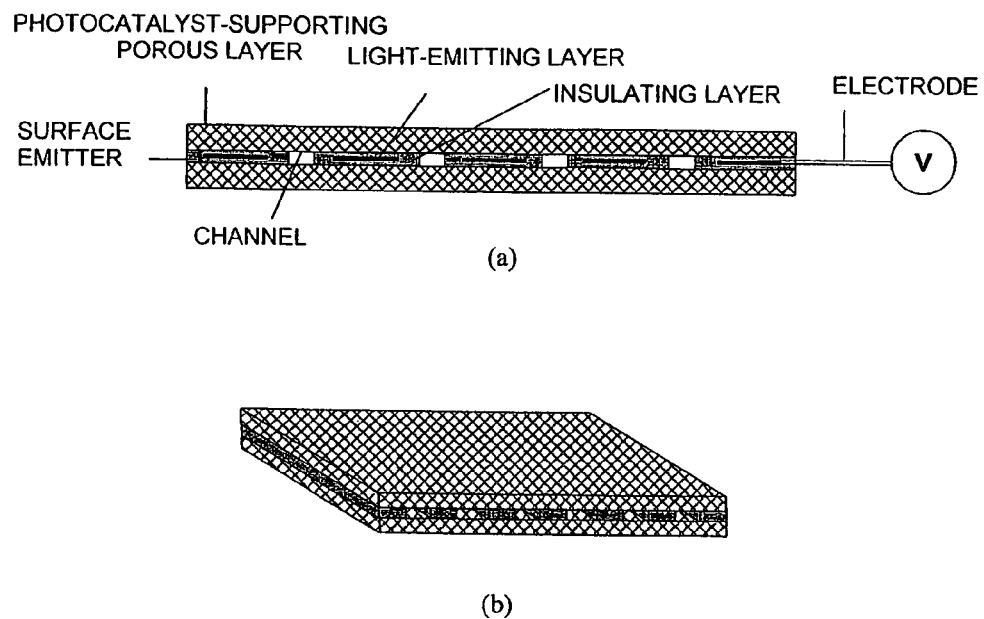
FIG. 1 is a diagram showing an example of a structure of the surface light-emitting device of the present invention, wherein (a) is a side view and (b) is a perspective view.

An example of the specific structure (a first structure) of the surface light-emitting device of the present invention is shown in FIG. 1. FIG. 1(a) is a side view, and FIG. 1(b) is a perspective view.

The surface light-emitting device in FIG. 1 is provided with porous layers that contain a photocatalyst and are formed on the top and bottom surfaces of a surface emitter. In the emitter, multiple rectangular light-emitting layers are aligned at fixed gap intervals. A treated fluid flows in through the surface of one porous layer, passes through the gaps in the surface emitter, and escapes through the porous layer on the opposite side. The visible light or ultraviolet light emitted from the surface emitter is incident perpendicular to the surfaces of the porous layers on the top and bottom surfaces of the surface emitter, and is repeatedly reflected in the porous layers. Therefore, the light can radiate uniformly throughout the entire porous layers, and the photocatalyst can be excited. The fluid that has passed through the porous layer on one surface then passes through the gaps in the surface emitter, and is finally ejected as a clarified fluid through the porous layer on the other surface. Fluid permeability increases with an increase in the surface area occupied by the gaps in the surface emitter in relation to the surface area of the entire top and bottom surfaces of the surface emitter (referred to herein as the channel surface area ratio), but an increase in the surface area of the gaps causes the surface area of the light-emitting portion to decrease and the porous structure containing the photocatalyst to not be uniformly exposed to light; i.e., brightness to be reduced. Generally, the surface area ratio of the channels is preferably 30 to 70% of the entire surface area.

The surface emitter preferably has no electrode portion and is electrically insulated from the exterior, as shown in FIG. 1. This results in a device that can be used with all kinds of liquids having high electrical conductivity.

A cross section provided with through-holes is also electrically insulated at this time. One example of the method for sealing the cross section is a method of temporarily creating an EL sheet provided with through-holes, pouring a liquid resin into the through-holes, drying the resin, and forming through-holes again in the resin while maintaining electrical insulation.

The surface light-emitting device of the present invention can be insulated without incurring extra costs because fluid does not pass through the light-emitting layer (this is ensured by forming through-holes that define channels for fluid flow). Furthermore, forming through-holes has the advantage of allowing the heat produced during light emission to be quickly discharged via the through-holes.

Figure 2:
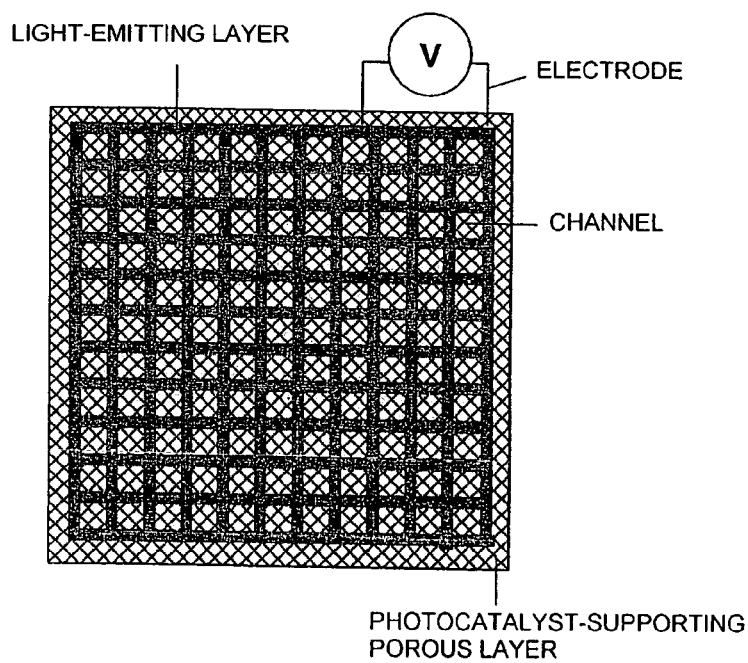
FIG. 2 is a diagram showing another structural example of the surface light-emitting device of the present invention.

In a second structure of the surface light-emitting device of the present invention, the light-emitting layers are disposed in a lattice pattern, as shown in FIG. 2.

In the case of rectangular light-emitting layers, groups of lead wires for applying voltage must be formed for each of the multiple light-emitting layers, but a lattice pattern has the effect of reducing costs because only one group of lead wires is needed. A lattice structure is preferred because light is more uniformly conducted into the porous structure. In this case, the size of the lattice acting as the channels is preferably 5 mm or less. The channels are not limited to this shape and may also be square or circular.

Also commercially available are EL sheets that have multiple circular holes formed in advance and that are intended as displays or backlights, and these sheets may therefore also be used.

In the present invention, light emitted from the light-emitting layer can be concentrated in the channels by controlling the structure of the surface emitter.

The top and bottom surfaces (the surfaces provided with porous layers) of the light-emitting layers may be enclosed by metal materials or other members that reflect but do not transmit visible light or ultraviolet light, in which case the light from the light-emitting layers is repeatedly reflected by and trapped within these members. The light is not discharged to the top and bottom surfaces but is concentrated in the channels via the cross section of the light-emitting layers (the surfaces adjacent to the channels), and the light is then discharged from the channels to the exterior. Specifically, with this type of structure, the device can be designed so that only the channels emit light. This type of structure can be easily obtained by selecting a metal material that reflects but does not transmit visible light or ultraviolet light, and using the material for the electrodes of the organic EL device used as the surface emitter, for example.

It is apparent that in a device in which porous layers having a photocatalyst are disposed on the top and bottom of the surface emitter, the portions of the porous layers directly above the channels are primarily the areas that allow the passage of fluid. Concentrating light in these portions makes it possible to attain the most efficient photocatalytic performance. In this type of light-condensing structure, a porous structure having a photocatalyst is embedded not only in the top and bottom of the surface emitter, but also in the portions of the channels formed, whereby an advantage is obtained of preventing light loss because the light-emitting source and the photocatalyst are at a distance of closest approach. With this type of structure, the size of the lattice serving as the channels does not need to be 5 mm or less. This is because light is concentrated in the channels.

With this type of structure, the photocatalyst that is in direct contact with the cross section of the light-emitting layer of the channels is directly irradiated with visible light or ultraviolet light that does not pass through an intervening space. The photocatalyst has the following problem. Specifically, when the photocatalyst is placed in a highly contaminated substance, the contaminants adhere strongly to the surface of the photocatalyst, and the light from the external light source does not reach the photocatalyst, impairing the photocatalytic function. In the surface light-emitting device of the present invention, a porous structure containing a photocatalyst is loaded into the channels. The above problem can therefore be resolved because visible light or ultraviolet light is continuously directed without passing through an intervening space onto the photocatalyst in direct contact with the cross section of the light-emitting layer of the channels.

The porous structures that have a photocatalyst and are packed into the channels may be porous structures that have a photocatalyst supported thereon, or porous structures having a photocatalyst packed in the form of a lattice.

Using ultraviolet light that has a wavelength in the vicinity of 254 nm allows the filtering device to be made to function as a filter having a sterilizing effect similar to that of a regular mercury lamp, even without a photocatalyst.

The first electroluminescent structure used in the present invention is commonly referred to as a dispersive EL, and the light-emitting layers are configured so that a phosphor that emits visible light or ultraviolet light is dispersed within a dielectric material.

The second structure is referred to as a thin-film EL and is a structure in which thin-film light-emitting layers that are 1 μm or less in thickness are enclosed by insulating layers, and the light-emitting layers are composed of only a phosphor and do not contain a resin.

A thin-film EL is characterized in emitting very bright light. Therefore, a large amount of light can be emitted and photocatalyst can be efficiently excited. However, a thin-film EL has drawbacks in that a large amount of power is consumed because of a low light-emitting efficiency of 1 lm/W or less, and this EL also requires an expensive gas-phase synthesis apparatus. A dispersive EL, on the other hand, sometimes has low brightness but a light-emitting efficiency in excess of 10 lm/W, and also has much lower manufacturing costs because power consumption is low and a powder application process is used.

An organic EL device or an inorganic EL device can be used as the surface emitter, but an organic EL device is preferably used due to having superior ultraviolet light resistance and other such durability characteristics.

Generally, an inorganic EL device is configured primarily from a light-emitting layer composed of fluorescent particles of ZnS or the like dispersed within a dielectric resin, and an insulated layer composed of $BaTiO_3$ or another such highly dielectric ceramic dispersed in a dielectric resin, wherein the light-emitting layer is enclosed by insulating layers, and electrodes are formed on the insulating layers.

Figure 3:
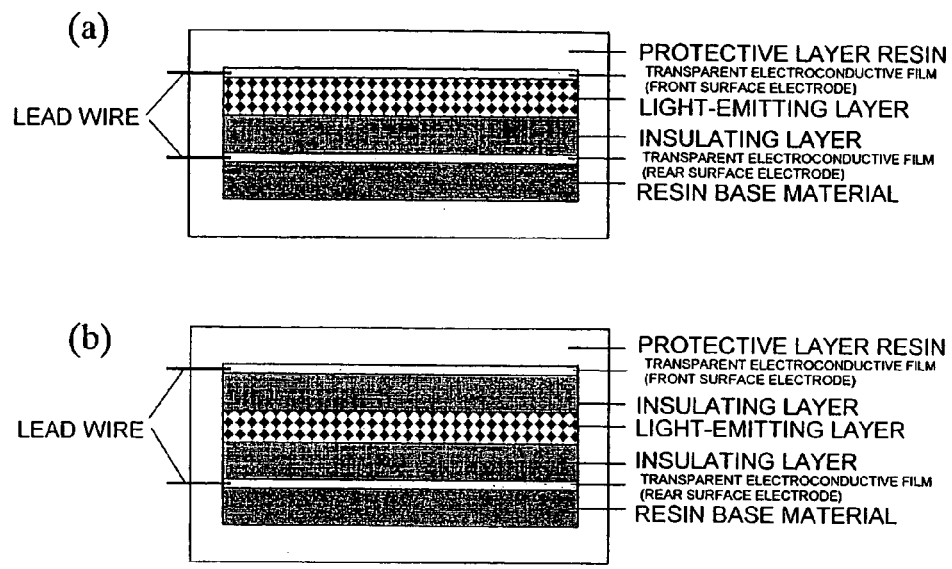
FIG. 3 is a diagram showing an example of the structure of the inorganic EL device used in the present invention.

A structural example of the inorganic EL device used in the present invention is shown in FIG. 3. In FIG. 3(a), an insulating layer is formed only on the bottom surface of the light-emitting layer, and in FIG. 3(b), insulating layers are formed on both the top and bottom surfaces of the light-emitting layer. In the present invention, both the front and back surface electrodes can be formed from a transparent electroconductive film. Specifically, the front and back surface electrodes are both formed from a transparent electroconductive film in cases in which porous layers having a photocatalyst that emits light due to ultraviolet light are placed on the top and bottom surfaces of the surface emitter. A resin base material and a protective layer resin are translucent with respect to light having the wavelength emitted by the surface emitter, and these two members also have electrically insulating properties.

The resin has low UV transmissivity if the wavelength of the emitted light is that of ultraviolet light. Polyethylene (PET) resins, which are regularly used, have low transmissivity with respect to ultraviolet light having a wavelength of 360 nm or less, and it is therefore preferable to use a UV transmitting resin in cases in which the wavelength of the emitted light is less than 360 nm. One example of a UV transmitting resin is Acrylite, made by Mitsubishi Rayon Co., Ltd. Since resins tend to degrade more with a reduction in the wavelength of the emitted light, this approach has an advantage in that all of the structural members can be made from inorganic materials without the use of a resin.

Figure 4:
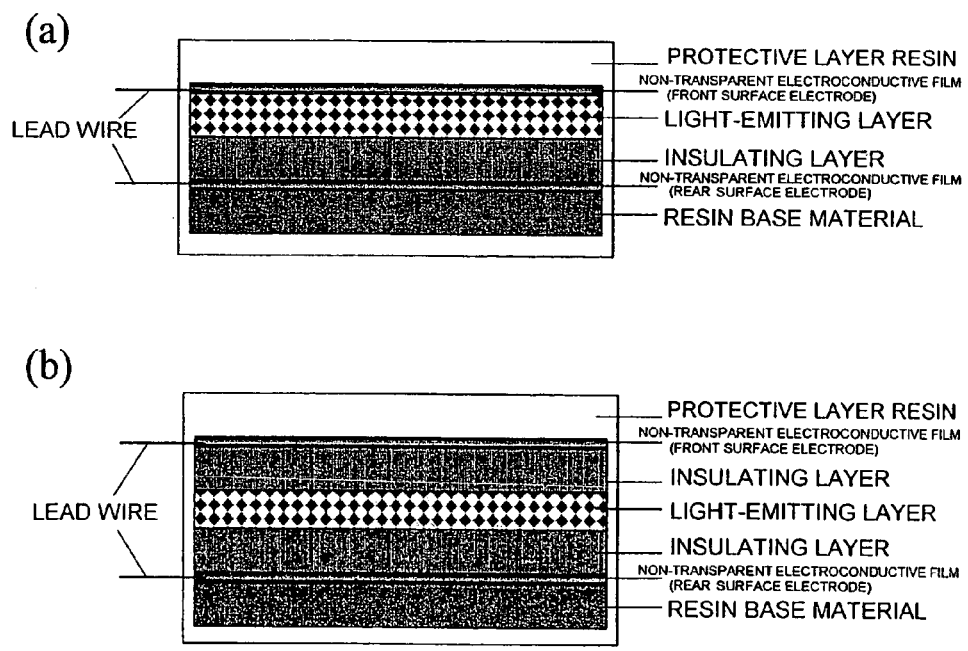
FIG. 4 is a diagram showing another structural example of the inorganic EL device used in the present invention.

A metal material or the like that reflects and does not transmit visible light or ultraviolet light may be used as the front and back electrodes instead of a transparent electroconductive film (see FIG. 4), in which case light from the light-emitting layers is repeatedly reflected and trapped by the electrodes. The light is not discharged to the top and bottom surfaces but is transmitted by the cross section of the light-emitting layers, is concentrated in the channels, and is then discharged to the exterior from the channels. In this case, the protective layer resin on the front and back surfaces does not need to be transmissive with respect to light having the wavelength emitted by the surface emitter, but the protective layer resin on the cross section must at least be transmissive and electrically insulated.

Any type of phosphor may be used for electroluminescence. The following phosphors can be used, for example.

A photocatalyst responsive to visible light can be excited in cases in which the wavelength of the light emitted by the surface emitter peaks at 540 nm or less. In the case of an inorganic EL device, ZnS doped with Cu, Cl, Al, or the like has high light-emitting efficiency and is therefore preferably used as the phosphor capable of emitting light at this wavelength. These phosphors have peak wavelengths in the vicinity of 450 to 540 nm, emit blue to green light, and can excite a photocatalyst responsive to visible light, but light having a peak wavelength of 460 nm or less is preferred for the ability of this light to excite the photocatalyst more efficiently.

The general formula is $Zn_{(1-x)}A_xS:Cu, D$ (wherein A is at least one type of 2A group element selected from among Be, Mg, Ca, Sr, and Ba; D is at least one type of element selected from among 3B group elements or 7B group elements; and the value of x is $0<x<1$), and a material that contains a phosphor having a function for emitting Blue-Cu light can be used. Al, Ga, Cl, F, and the like are possible examples of D, but Al and Cl are preferred in terms of raw material costs. The value of x is preferably $0.25 \leq x \leq 0.6$.

The Blue-Cu emitted light is described hereinbelow. For example, in the phosphor (ZnS: Cu, Cl), doped Cu is generally substituted in place of Zn, while Cl is substituted in place of S. Since the wavelength of the emitted light is in the vicinity of 530 nm, indicating green, the light is referred to as Green-Cu light. The Cu may enter the gaps in the ZnS crystal lattice, and the Cu may be substituted in place of Zn. The resulting emitted light will be Blue-Cu light with a short wavelength in the vicinity of 460 nm. Using Cu for doping causes part of the added Cu to remain in the phosphor as highly conductive $Cu_2S$, and when an AC electric field is applied to an EL device obtained using this phosphor, EL light is emitted because of the concentration of the electric field in the periphery of the conductive $Cu_2S$, and for other reasons. The wavelength of this emitted light depends on the band gap of the semiconductor that is the source of the phosphor, and the wavelength of the emitted light decreases with larger band gaps. Consequently, it is possible to use, e.g., ZnS: Cu, Cl, Al (450 to 460 nm), or $Zn_{0.8}Mg_{0.2}S:Cu, Cl, Al$ (410 to 430 nm) can be used if Blue-Cu light is used.

The phosphor is preferably a UV-emitting phosphor, wherein the peak wavelength of the emitted light is less than 400 nm, or preferably 300 to 375 nm. In this case, it is possible to excite anatase $TiO_2$, which has the highest photocatalytic performance.

ZnS doped with Ag, Cl, Al, or the like is ideal as the phosphor that emits ultraviolet light. A phosphor containing at least one of Cu, Ag, Au, Li, Na, N, As, P, and Sb, which forms an acceptor level in a semiconductor; and at least one of Cl, Al, I, F, and Br, which forms a donor level in the semiconductor, is preferred because of the high light-emitting efficiency of these elements. In particular, this semiconductor may or may not partially contain ZnS as a primary component, and a Group II-IV compound semiconductor (MgS, CaS, SrS, BeS, BaS, or the like) as a secondary element.

The general formula is $Zn_{(1-x)}A_xS:Ag, D$ (wherein A is at least one type of 2A group element selected from among Be, Mg, Ca, Sr, and Ba; D is at least one type of element selected from among 3B group elements or 7B group elements; and the value of x is $0<x<1$), and a phosphor having a function for emitting Blue-Cu light can be preferably used. Al, Ga, Cl, F, and the like are possible examples of D, but Al and Cl are preferred in terms of raw material costs. The value of x is preferably $0.25 \leq x \leq 0.6$.

The light-emitting mechanism of the phosphor is identical to that of ZnS:Cu, Cl, and is referred to as Blue-Cu emitted light even in cases in which Ag is doped. For example, ZnS: Ag, Cl, Al (399 nm) or $Zn_{0.8}Mg_{0.2}S:Ag, Cl, Al$ (369 nm) can be used. In the case of Ag, $Ag_2S$ is formed similar to the case of Cu, but since electrical conductivity is low, EL light is not emitted because no electric field is concentrated. Consequently, in the case of Ag, EL light can be emitted if the resulting phosphor is compounded with a $Cu_2S$ phase or another electroconductive material by means of another method.

Another example of an ideal material is $ZnF_2:Gd$, which reflects ultraviolet light having a strong emission line spectrum of 311 nm. The brightness of the emitted light is further improved when Pr is doped together with Gd. Calcium sulfide is also known as a phosphor that emits light efficiently by electron beam excitation. Examples include CaS: Gd, F (emits light at 315 nm), CaS: Cu (emits light at 400 nm), and CaS: Ag, K (emits light at 388 nm). Calcium oxide is also known as a phosphor that efficiently emits light with electron beams, despite lacking chemical stability in the atmosphere. Examples include CaO: F (emits light at 335 nm), CaO: Cu (emits light at 390 nm), and CaO: Zn, F (emits light at 324 to 340 nm).

In regular electroluminescence elements, the threshold voltage for emitting light is estimated at about $1\times10^4$ to $1\times10^6$ V/cm, but the threshold voltage can be reduced by creating a structure in which the light-emitting particles are covered with a highly dielectric material.

The wavelength of the emitted light is preferably 350 nm or less because the photocatalyst can then be excited with maximum efficiency at this wavelength.

A resin or a ceramic is used as the dielectric material. The same resin as is found in regular EL devices may be used for a material that emits visible light having a wavelength in excess of 360 nm. A Cyanoresin (made by Shin-Etsu Chemical Co., Ltd.) or the like can be used as a dielectric resin. At shorter wavelengths, however, it is preferable to use a dielectric ceramic instead of a resin because a dielectric resin may degrade over time. Examples of a dielectric ceramic include $BaTiO_3$, $SrTiO_3$, $PbTiO_3$, and other highly dielectric materials.

Either a dielectric ceramic dispersed in a resin, or a dielectric ceramic alone is used as the insulating layer.

A photocatalyst responsive to visible light can be excited in cases in which the light emitted by the surface emitter has a peak wavelength of 540 nm or less. The photocatalyst responsive to visible light is preferably $TiO_2$: S, $TiO_2$: N, or the like.

An anatase $TiO_2$ photocatalyst, which has the highest photocatalytic performance, can be excited in cases in which the emitted light has a peak wavelength of 400 nm or less. It is preferable that the photocatalyst be primarily crystalline anatase $TiO_2$, but the photocatalyst may also be crystalline rutile or brookite, which is also crystalline.

Any material can be used as the porous layer and porous structure as long as through-holes are formed in the material, but a foamed metal, a foamed ceramic, a woven resin fabric, or the like is preferred. These materials have high porosity and excellent transmissivity. A photocatalyst can be supported on these materials. A porous structure composed of a highly refractive material is more preferred in order to uniformly guide light into a porous structure having a photocatalyst. For example, there are methods for forming the porous structure from titanium oxide itself, which is highly refractive. The porous layer and the porous structure preferably have small pore diameters because light is then repeatedly reflected within the porous structure. Ideally, the average pore diameter is 500 μm or less. The pore diameter in the porous structure can be measured with a mercury porosimeter or the like. The pore diameter has no lower limit in particular, but ideally the lower limit is about 0.005 μm because the permeation resistance of the fluid increases as the pore diameter decreases.

The photocatalyst is preferably supported on the porous structure by means of the sol-gel process. This is because the photocatalytic effects increase with an increase in the specific surface area of the porous structure.

A thin surface light-emitting device can be made by reducing the thickness of the porous layer.

The surface light-emitting device of the present invention can be used as a filtering device, and the entire device is preferably made as thin as possible in cases in which the filtering device is used as a filter in an air purifier or a filter for an air conditioner. Ideally, the thickness of the EL sheet is 1 mm or less, the thickness of the porous layer having a catalytic function is 1 mm or less, and the entire device (the sum of the EL sheet and the porous structure for supporting the photocatalyst) is 3 mm or less in thickness.

Figure 5:
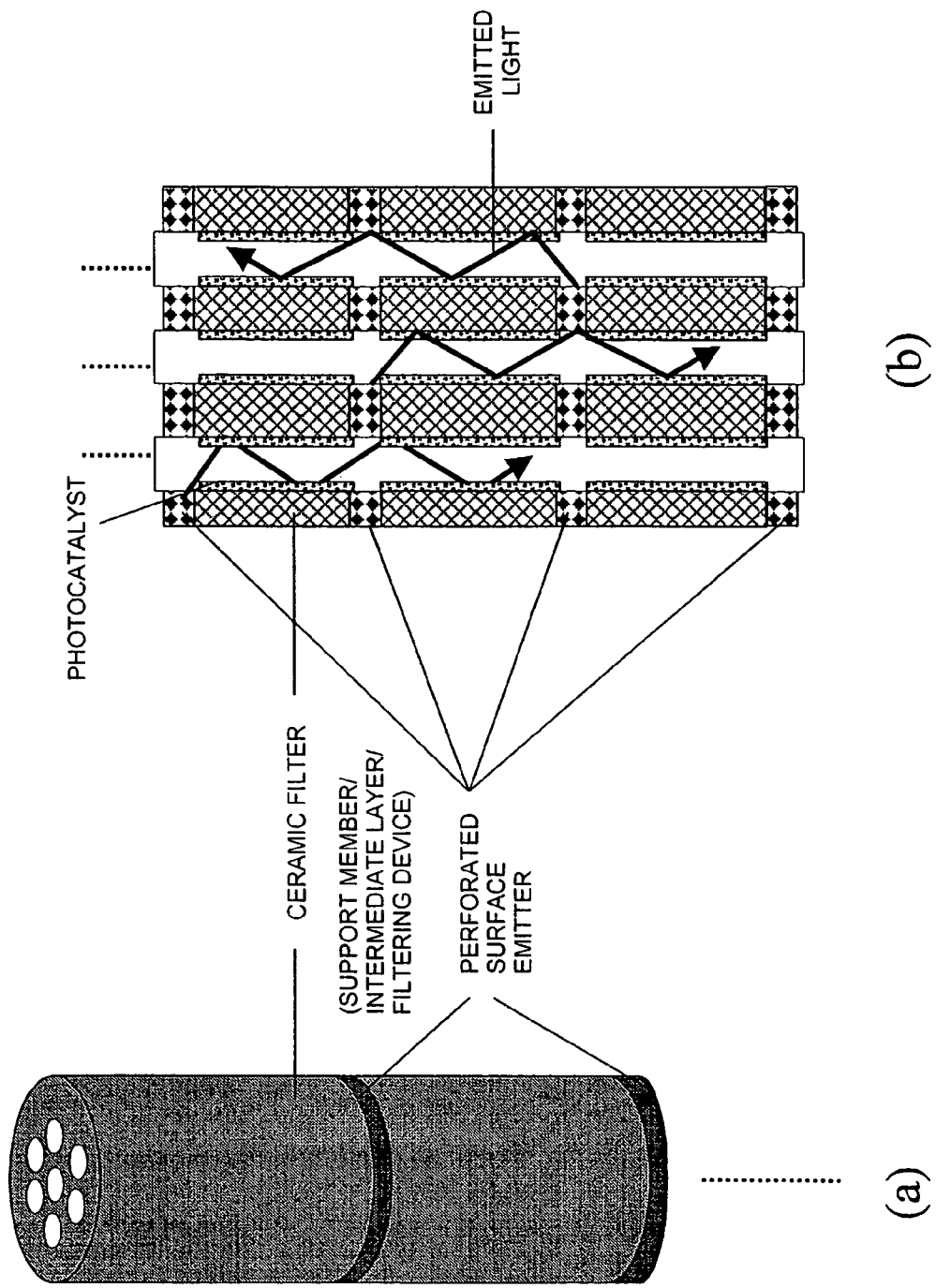
FIG. 5 is a diagram showing another structural example of the surface light-emitting device of the present invention.

A ceramic filter can be used as the porous layer. FIG. 5 shows a specific structural example of a case in which a ceramic filter is used as the porous layer. FIG. 5(*a*) is a perspective view, and FIG. 5(*b*) is a cross-sectional view of a surface parallel to the direction in which the feed solution flows.

The structure is obtained substantially by stacking a ceramic filter that primarily cleans fluids by cross-flow filtration, and a surface light-emitting sheet in which the channels in the ceramic filter are communicated with the channels in the surface emitter. The surface light-emitting sheet has through-holes that preferably have the same cross-sectional shape as those in the ceramic filter. In the structural example in FIG. 5, the photocatalyst is formed as a photocatalytic layer on the inner walls of the channels in the ceramic filter.

In this case, the light emitted from the light-emitting layers can be concentrated in the channels by controlling the structure of the surface emitter. The light directed into the channels expands throughout the channels while being repeatedly absorbed and reflected by the inner walls of the channels; i.e., by the photocatalytic layer formed on the surface of the filtration layer. The photocatalyst is excited in a successive manner.

In cases in which an inorganic EL sheet is used as described above, the method whereby the light emitted from the light-emitting layers of the surface emitter is concentrated in the channels involves enclosing the top and bottom surfaces of the light-emitting layers (the surfaces provided with ceramic filters) with metal material or other such members that reflect and do not transmit or absorb visible light or ultraviolet light, in which case the light from the light-emitting layers is repeatedly reflected and trapped by these members. The light is not discharged to the top and bottom surfaces, but is instead concentrated in the channels through the cross sections of the light-emitting layers (the surfaces near the channels). With an inorganic EL device, the top and bottom electrodes can be easily created by using aluminum, gold, or another such metal material for the electrodes.

In one example of the method for forming the photocatalytic layer, a liquid containing dispersed titanium oxide particles is filtered with a ceramic filter, a sedimentary layer of titanium oxide particles is formed on the surface of the filtration layer, and the resulting formation is heated and baked so that the particles are moderately sintered together. The titanium oxide may be similarly filtered by adjusting the viscosity of an alkoxide solution of titanium that has formed after baking the titanium oxide, and the titanium oxide may be baked again. The filtration layer of the ceramic filter may be formed from titanium oxide.

The photocatalyst may also be supported on a carrier member instead of the inner walls of the channels. In this case, the surface emitter may, e.g., be an inorganic EL element so that light is not concentrated in the channels but is emitted to the top and bottom of the surface emitter. The electrodes can then be formed from a transparent electroconductive thin film of an indium and tin-based oxide (ITO) or ZnO or the like. The method for supporting the photocatalyst in this case involves forming a carrier member by immersing the carrier member in a liquid obtained by adjusting the viscosity of an alkoxide solution of titanium that has formed after baking the titanium oxide, and removing the carrier member out of the liquid and baking the carrier member.

The surface light-emitting device of the present invention can have a stacked structure in which surface emitters and porous layers are repeatedly stacked.

In cases in which the surface light-emitting device of the present invention is used as a filtering device, relatively large particles, such as those suspended in air, for example, are physically collected on the surfaces of the porous layers having photocatalysts, and smaller particles are decomposed by the photocatalysts in the process whereby the particles pass through the porous layers having photocatalysts. Therefore, repeating the stacked structure of surface emitters and porous layers results in a highly reliable filter, but also has drawbacks in that permeability is reduced.

Next, the optically assisted ceramic filter of the present invention will be described.

The optically assisted ceramic filter of the present invention is a ceramic filter that primarily cleans liquids by cross-flow filtration. The term "cross-flow filtration" refers to a form of filtration in which a feed solution is circulated while the treated solution is recovered in a direction perpendicular to the flow of the feed solution.

Figure 6:
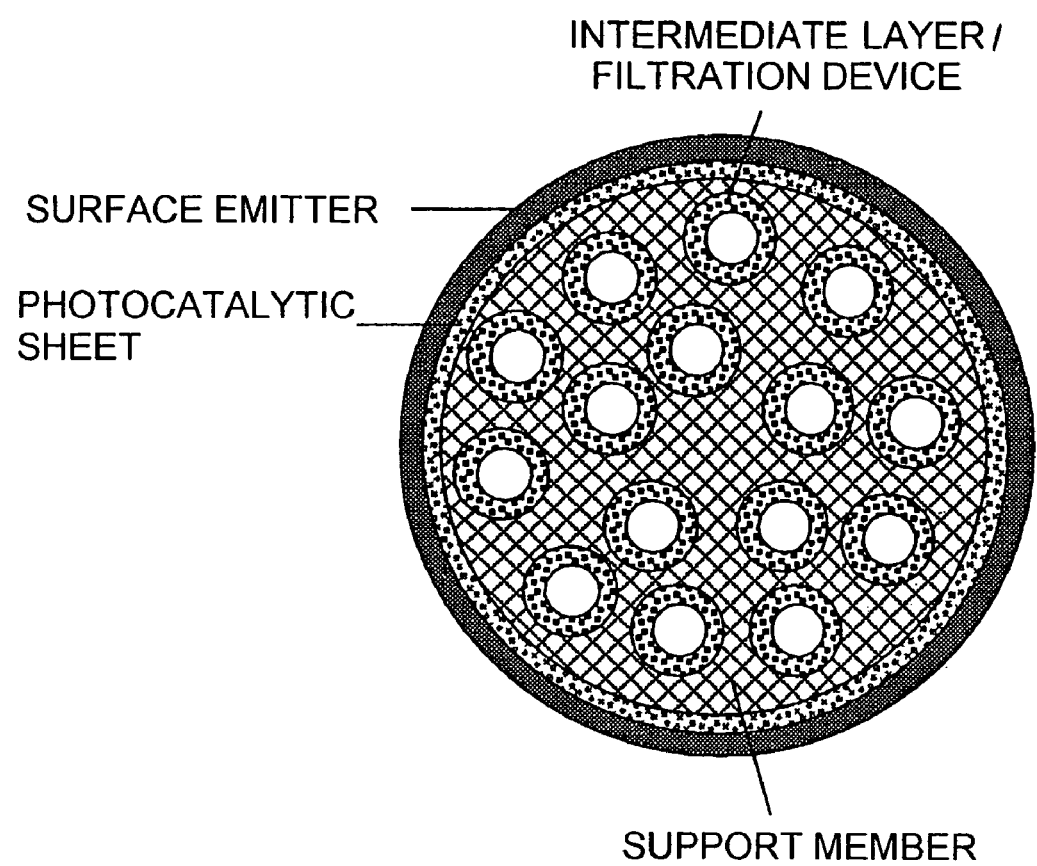
FIG. 6 is a diagram showing a structural example of the optically assisted ceramic filter of the present invention.

FIG. 6 shows a specific example of a first structure of the optically assisted ceramic filter of the present invention.

The structure is essentially composed of a ceramic filter and a surface light-emitting sheet in which channels are perpendicular to the cross section. The structure also has a photocatalytic sheet (photocatalytic layer). The ceramic filter is composed of a filtration layer for performing filtration, an intermediate layer, and a carrier member. The photocatalytic sheet is aligned with the cross-sectional shape of the ceramic filter, and is wrapped around the side surface of the ceramic filter. The term "the cross section of the ceramic filter" in the present invention refers to the cross section that is perpendicular to the flow of the feed solution, and the term "side surface" refers to the surface other than the bottom surface on the front of the cylindrical ceramic filter.

The clarified fluid that has passed through the filtration layer is then discharged from the side surface of the ceramic filter and caused to impregnate the photocatalytic sheet. Light emitted from the surface emitter excites the photocatalyst in the photocatalytic sheet to create a photocatalytic effect, and organic substances, bacteria, viruses, and other such substances in the clarified fluid that could not be collected or decomposed by filtration are decomposed or destroyed.

After being subjected to the decomposition and sterilization treatment, the fluid is recovered from the interior of the photocatalytic sheet, along the inner surface, and from the end of the ceramic filter. In cases in which multiple through-holes are formed in the surface light-emitting sheet in a direction perpendicular to the surface of the surface emitter (in a direction perpendicular to the side surface of the ceramic filter), the fluid that has undergone decomposition and sterilization treatment can be discharged to the exterior via these through-holes. The amount of fluid that can be recovered is therefore greater than in cases in which no through-holes are formed. Conversely, through-holes must be formed in the surface light-emitting sheet in cases in which the permeability of the ceramic filter must be increased.

The surface light-emitting device having through-holes according to the present invention can be used as a surface light-emitting device that has through-holes.

The photocatalytic sheet is composed of a photocatalytic powder supported on the surface of a resin, metal, or ceramic porous structure. The sheet may be obtained by forming a coating of a photocatalytic film. The side surface of the ceramic filter may be coated with a photocatalyst. Titanium oxide is a common photocatalyst. Therefore, the light emitted by the surface emitter must have a wavelength that lies within a wavelength band capable of exciting the photocatalyst. Light having a peak wavelength of 460 nm or less is preferred in the case of a photocatalyst responsive to visible light. Photocatalytic performance is sometimes observed if the wavelength exceeds 460 nm, but the performance is reduced. The light preferably has a peak wavelength of 400 nm or less in the case of anatase titanium oxide, which is a photocatalyst responsive to ultraviolet light. Photocatalysts responsive to ultraviolet light generally exhibit better performance in terms of photocatalytic action.

In an optically assisted ceramic filter, the surface emitter must be flexible and capable of bending because the surface emitter must be wrapped around the side surface of the ceramic filter. An organic EL sheet, inorganic EL sheet, or other such sheet is therefore preferred. A dispersive inorganic EL sheet is preferred in order to allow low-cost manufacturing of a surface emitter in which multiple through-holes are formed perpendicular to the surface of the surface emitter. The term "dispersive inorganic EL" refers to the concept of forming light-emitting layers having phosphor dispersed in a dielectric resin on the surface of a resinous substrate sheet by screen printing, the doctor blade method, or another such method, and causing light to be emitted by applying an AC electric field to the electrodes formed on the top and bottom of the light-emitting layers. Inorganic EL is also preferred because of its high moisture resistance. Although it is difficult for ultraviolet light to be emitted with organic EL, organic EL has an advantage with visible light in that a high degree of brightness is obtained more easily than with inorganic EL. Inorganic EL has problems with a short service life when used in water because of its low moisture resistance.

An organic EL or inorganic EL device can be used as the surface emitter, but an inorganic EL device having excellent UV resistance and other such durability characteristics is preferred in the case of ultraviolet light having a peak wavelength of 400 nm or less. As described above, the principal structural elements of an inorganic EL surface emitter are usually light-emitting layers in which particles of ZnS or another such phosphor are dispersed in a dielectric resin, and insulating layers wherein $BaTiO_3$ or another such highly dielectric ceramic is dispersed in a dielectric resin. Electrodes are formed on the insulating layers. The resin easily degrades when the wavelength of the emitted light is that of ultraviolet light. It is therefore advantageous in this case to use inorganic materials for all of the structural components instead of using a resin. However, since the resin often degrades with ultraviolet light primarily having a wavelength of 350 nm or less, a resin may be used in cases not involving ultraviolet light in this wavelength range.

The light emitted from the light-emitting layers can be concentrated on the side of the photocatalytic sheet by controlling the structure of the surface emitter. For example, an inorganic EL device can be provided with a structure in which light is emitted only inward (towards the light-emitting layers). This can be achieved by forming the outward-facing electrodes from aluminum, gold, or another such metal material.

The same phosphor as is used in the surface light-emitting device described above can be used as the phosphor in the surface emitter.

The optically assisted ceramic filter of the present invention primarily cleans liquids by cross-flow filtration, but gases may also be filtered. The term "cross-flow filtration" refers to a form of filtration in which a feed solution is circulated while the treated solution is recovered in a direction perpendicular to the flow of the feed solution. If the optically assisted ceramic filter of the present invention is used, the bacteria or organic matter that could not be collected by physical filtration can be decomposed or destroyed by the photocatalytic action.

EMBODIMENTS

The present invention is described in further detail hereinbelow by means of embodiments.

First Embodiment

1. Preparation

Protective Layer Resin

A transparent resin sheet (trade name: Acrylite S, product #000, Mitsubishi Rayon Co., Ltd.) 100×100 mm in size and 100 μm in thickness was prepared. Lattice-shaped holes of various sizes were formed in this sheet in advance at intervals (a pitch) of 4 mm.

Insulating Layer $BaTiO_3$: average grain size: 0.2 μm

Resin: made by Shin-Etsu Chemical Co., Ltd. (trade name: Cyanoresin)

Phosphor

ZnS: Cu, Cl powder average grain size: 3 μm peak wavelength of emitted light: 533 nm (green)

ZnS: Cu, Cl, Al powder average grain size: 3 μm peak wavelength of emitted light: 450 nm (blue)

ZnS: Ag, Cl powder average grain size 3 μm peak wavelength of emitted light: 380 nm (ultraviolet light)

Porous Structure

An SiC porous structure was used, having a size of 120×120 mm, a thickness of 0.1 mm, and a porosity of 50% with the various average pore diameters shown in Table 1.

Photocatalyst

Anatase $TiO_2$ average grain size: 0.03 μm (commercially available)

$TiO_2$: S average grain size 0.03 μm

Thiourea ($CH_4N_2S$) powder and $Ti(OC_3H_7)_4$ were mixed in ethanol, and were concentrated in a vacuum until a white slurry was formed. The slurry was baked for 2 hours at 588° C. under atmospheric conditions to obtain a powder. The amount of doped S in relation to oxygen was 2 at %.

2. Steps

Figure 7:
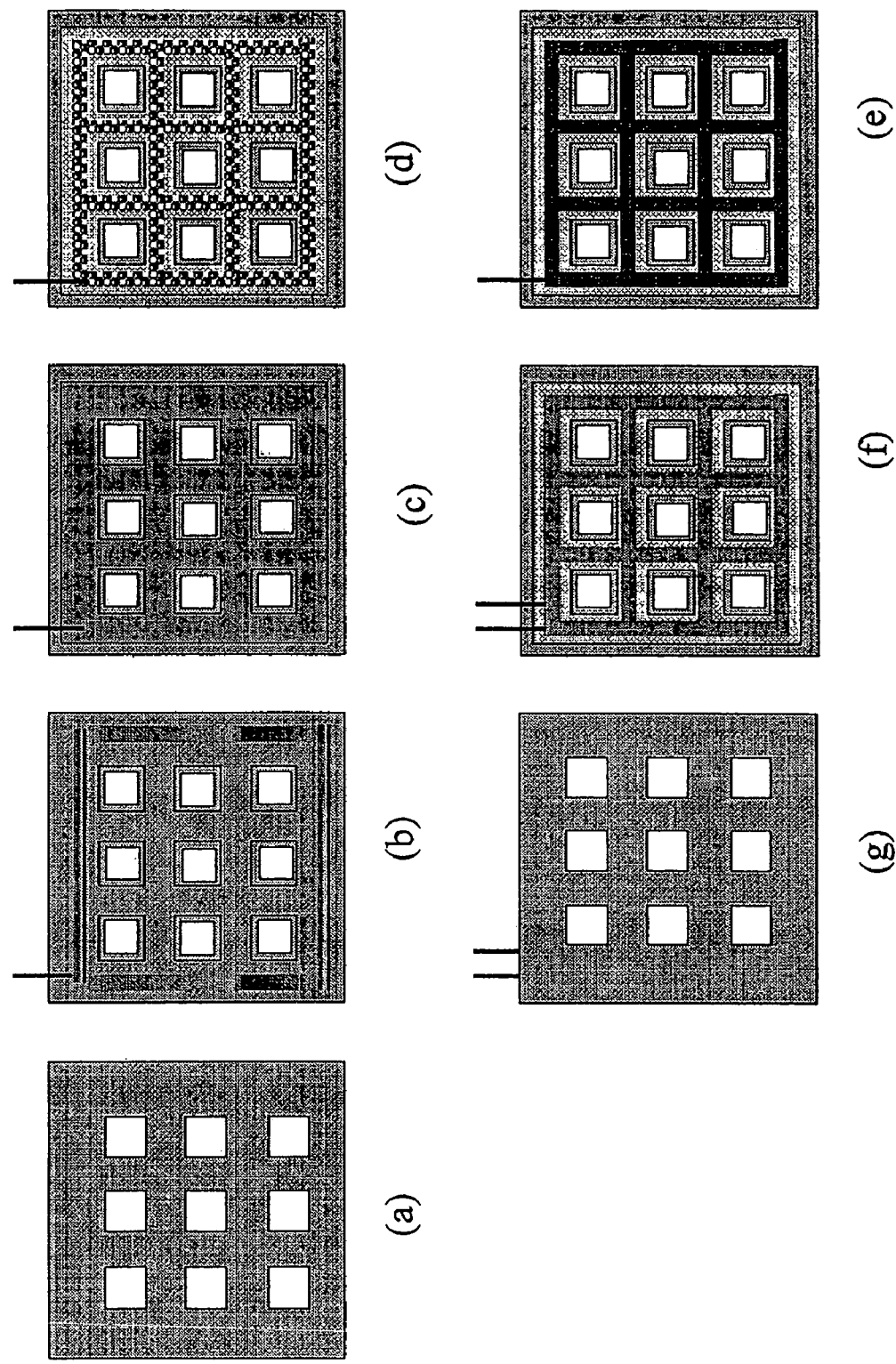
FIG. 7 is a diagram showing the steps of manufacturing the surface light-emitting device in the embodiments.

A surface light-emitting device was manufactured as shown in FIG. 7 by following the steps hereinbelow.

(1) Formation of Electrode 1

The protective layer resin (FIG. 7(a)) was coated by sputtering with aluminum in a lattice pattern having a line width of 50 μm and a thickness of 0.1 μm, and an electrode lead wire was attached (FIG. 7(b)). The entire lattice-patterned sheet was then coated with a 0.1-μm transparent electroconductive film (ITO) (FIG. 7(c)).

(2) Formation of Inner Insulating Layer

The resin (made by Shin-Etsu Chemical Co., Ltd. (trade name: Cyanoresin)) was dispersed and dissolved in an amount of 25 vol % relative to cyclohexanone, and a $BaTiO_3$ powder was dispersed (25 vol %) to form a slurry. A coating layer having a thickness of 30 μm was formed by screen printing on the electrode (FIG. 7(d)).

(3) Formation of Light-Emitting Layer

A resin (Cyanoresin) was dispersed and dissolved in an amount of 25 vol % relative to cyclohexanone. A slurry was formed by subjecting the pulverulent phosphor to a dispersion treatment (25 vol %) in this solution in an Ar gas. A coating layer having a thickness of 60 μm was formed by screen printing on the surface of the inner insulating layer (FIG. 7(e)).

(4) Formation of Electrode 2

The surface of the light-emitting layer was coated with a transparent electroconductive film in the same manner as the electrode 1, and an electrode lead wire was attached (FIG. 7(f)).

(5) Sealing

A sheet having the same shape as the protective layer resin used in (1) was overlaid, and was then thermocompression bonded and completely sealed (FIG. 7(g)). An epoxy resin was then applied over the cross section of the through-holes.

(6) Supporting the Photocatalyst

A solution was prepared by dispersing photocatalytic particles in alcohol, an SiC porous structure was immersed therein, and the structure was lifted out at a speed of 0.003 m/s. The resulting structure was then heated for 0.5 hours at 300° C. under atmospheric conditions, and the walls of the pores in the SiC porous structure were coated with photocatalytic particles. This process was repeated ten times.

(7) Stacking

An SiC porous structure for supporting a photocatalyst was disposed on the top and bottom surfaces of a surface light-emitting sheet, and the ends were screwed shut, resulting in a filtering device.

3. Evaluation (1) Photocatalytic Reaction Experiment 2,3',4,4',5-Pe-CB, a type of dioxin, was dissolved in water to prepare 3.0 L of a solution having a concentration of 55 pg/L. 5% of india ink solution was added in advance in order to intentionally color the water, so that the liquid was made to have high turbidity. The resulting liquid and the filtering device prepared as described above were placed in the apparatus shown in FIG. 8.

The resulting liquid was circulated at a flow rate of 0.3 L/min, while AC electric fields having the voltages and frequencies shown in Table 1 were applied between the electrodes. The time elapsed until the dioxin was completely decomposed was measured, with a maximum time of 100 hours.

Figure 9:
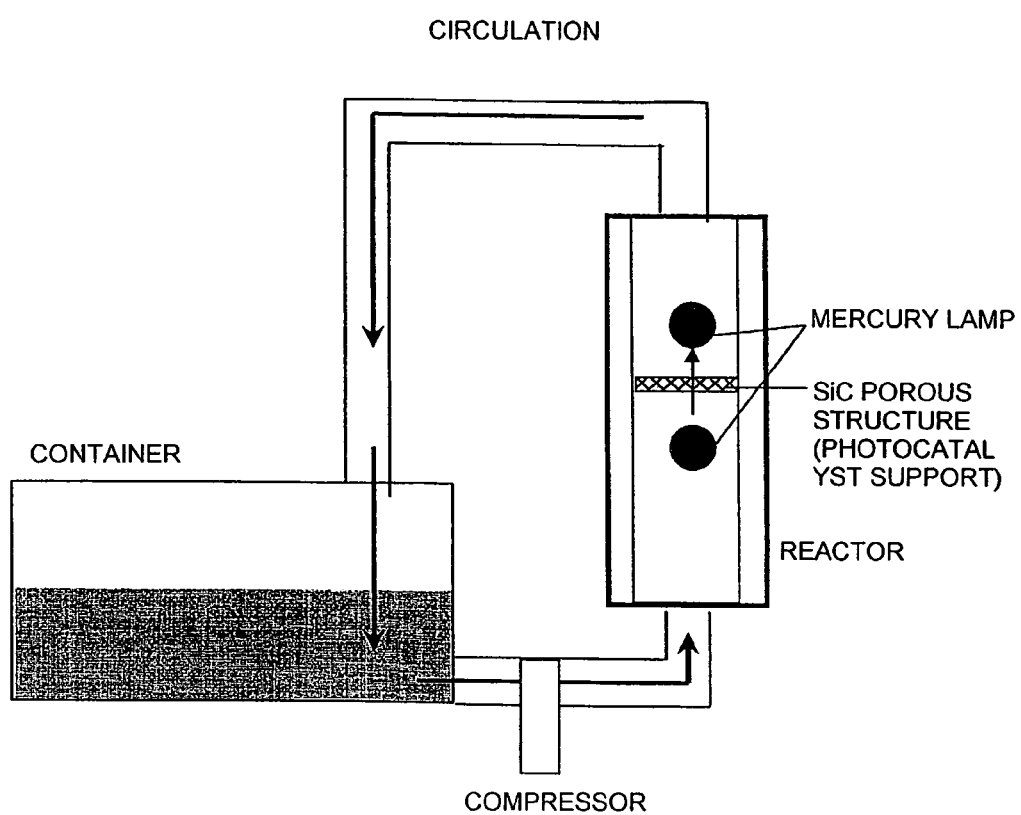
FIG. 9 is an explanatory diagram of a method for evaluating a surface light-emitting device in a comparative example.

As a comparative example, only SiC porous structures for supporting the photocatalysts shown in Table 1 were placed in the apparatus shown in FIG. 9, and the same photocatalytic reaction experiment as in the embodiment was conducted while a UV LED lamp having an emitted light wavelength of 360 nm and an output of 5 mW was illuminated from a distance of 50 mm.

The results are shown in Table 1.

TABLE 1

First Embodiment

| Average pore diameter of SiC porous structure (μm) | Porosity of SiC porous structure (%) | Lattice hole size (mm) | Pitch (mm) | Channel surface area ratio (%) | Inner insulating layer thickness (μm) | Light-emitting layer thickness (μm) | Type of phosphor | Voltage (V) | Frequency (Hz) | Wavelength of emitted light (nm) | Type of photocatalyst | Time of decomposition (hr) |
|---|---|---|---|---|---|---|---|---|---|---|---|---|
| 0.1 | 50 | 5 | 4 | 56 | 30 | 60 | ZnS: Ag, Cl | 120 | 550 | 380 | anatase $TiO_2$ | 6.3 |
| 1 | 50 | 1.5 | 4 | 27 | 30 | 60 | ZnS: Ag, Cl | 120 | 550 | 380 | anatase $TiO_2$ | 10.2 |
| 1 | 50 | 2 | 4 | 33 | 30 | 60 | ZnS: Ag, Cl | 120 | 550 | 380 | anatase $TiO_2$ | 8.6 |
| 1 | 50 | 5 | 4 | 56 | 30 | 60 | ZnS: Ag, Cl | 120 | 550 | 380 | anatase $TiO_2$ | 8.5 |
| 1 | 50 | 7.5 | 4 | 65 | 30 | 60 | ZnS: Ag, Cl | 120 | 550 | 380 | anatase $TiO_2$ | 10.6 |
| 1 | 50 | 10 | 4 | 71 | 30 | 60 | ZnS: Ag, Cl | 120 | 550 | 380 | anatase $TiO_2$ | 12.2 |
| 10 | 50 | 5 | 4 | 56 | 30 | 60 | ZnS: Ag, Cl | 120 | 550 | 380 | anatase $TiO_2$ | 23 |
| 400 | 50 | 5 | 4 | 56 | 30 | 60 | ZnS: Ag, Cl | 120 | 550 | 380 | anatase $TiO_2$ | 77 |
| 600 | 50 | 5 | 4 | 56 | 30 | 60 | ZnS: Ag, Cl | 120 | 550 | 380 | anatase $TiO_2$ | 99.5 |
| 0.1 | 50 | 5 | 4 | 56 | 30 | 60 | ZnS: Ag, Cl | 120 | 5000 | 380 | anatase $TiO_2$ | 3.6 |
| 1 | 50 | 5 | 4 | 56 | 30 | 60 | ZnS: Ag, Cl | 120 | 5000 | 380 | anatase $TiO_2$ | 6.4 |
| 10 | 50 | 5 | 4 | 56 | 30 | 60 | ZnS: Ag, Cl | 120 | 5000 | 380 | anatase $TiO_2$ | 18 |

TABLE 1-continued

First Embodiment

| Average pore diameter of SiC porous structure (μm) | Porosity of SiC porous structure (%) | Lattice hole size (mm) | Pitch (mm) | Channel surface area ratio (%) | Inner insulating layer thickness (μm) | Light-emitting layer thickness (μm) | Type of phosphor | Voltage (v) | Frequency (Hz) | Wavelength of emitted light (nm) | Type of photocatalyst | Time of decomposition (hr) |
|---|---|---|---|---|---|---|---|---|---|---|---|---|
| 1 | 50 | 5 | 4 | 56 | 30 | 60 | ZnS: Cu, Cl, Al | 120 | 550 | 450 | $TiO_2$: S | 44 |
| 1 | 50 | 5 | 4 | 56 | 30 | 60 | ZnS: Cu, Cl | 120 | 550 | 530 | $TiO_2$: S | 88 |
| * 1 | 50 | 5 | 4 | 56 | | | LED | | | 360 | anatase $TiO_2$ | 100< |

* Indicates a comparative example

The filtering device obtained using the surface light-emitting device of the present invention had a shorter decomposition time than a filter having an external light source. The reason for this is believed to be that only the polar surfaces of the $TiO_2$ porous structure were able to be excited in a filter having an external light source, because the emitted light is easily absorbed in a liquid having high turbidity.

The filtering device obtained using the surface light-emitting device of the present invention has a shorter decomposition time because the catalytic function acts uniformly over the entire $TiO_2$ porous structure layer while the emitted light is repeatedly scattered within this porous structure layer.

Second Embodiment (1) Preparation (Protective Layer Resin)

A transparent resin sheet (trade name: Acrylite S, product #000, Mitsubishi Rayon Co., Ltd.) 100×100 mm in size and 100 μm in thickness was prepared. Lattice-shaped holes having a size of 1 mm were formed on one side of this sheet in advance at intervals of 1 mm.

(Insulating Layer)

$BaTiO_3$: average grain size: 0.2 μm

Resin: made by Shin-Etsu Chemical Co., Ltd. (trade name: Cyanoresin)

Phosphor

ZnS: Ag, Cl powder; average grain size: 3 μm; peak wavelength of emitted light: 380 nm (ultraviolet light)

ZnS-20 mol % MgS: Ag, Cl powder; average grain size: 3 μm; peak wavelength of emitted light: 366 nm (ultraviolet light)

$ZnF_2$: Gd, Pr, Cu powder; average grain size: 3 μm; peak wavelength of emitted light: 311 nm (ultraviolet light)

Photocatalyst

Anatase $TiO_2$; average grain size: 0.03 μm (commercially available)

2. Steps

A surface light-emitting device was manufactured according to the First Embodiment by following the steps hereinbelow.

(1) Formation of Electrode 1

The protective layer resin was coated with 0.1 μm of aluminum by sputtering, and an electrode lead wire was attached.

(2) Formation of Inner Insulating Layer

The resin (made by Shin-Etsu Chemical Co., Ltd. (trade name: Cyanoresin)) was dispersed and dissolved in an amount of 25 vol % relative to cyclohexanone, and a $BaTiO_3$ powder was dispersed (25 vol %) to form a slurry. A coating layer having a thickness of 30 μm was formed by screen printing on the electrode.

(3) Formation of Light-Emitting Layer

A resin (Cyanoresin) was dispersed and dissolved in an amount of 25 vol % relative to cyclohexanone. A slurry was formed by subjecting the pulverulent phosphor to a dispersion treatment (25 vol %) in this solution in an Ar gas. A coating layer having a thickness of 60 μm was formed by screen printing on the surface of the inner insulating layer.

(4) Formation of Electrode 2

The surface of the light-emitting layer was coated with aluminum in the same manner as the electrode 1, and an electrode lead wire was attached.

(5) Sealing

A sheet having the same shape as the protective layer resin used in (1) was overlaid, and was then thermocompression bonded and completely sealed.

(6) Supporting the Photocatalyst

Photocatalytic particles were molded into a diameter of 1 mm and a thickness of 300 um by dry pressing, and a porous structure having a porosity of 65% was formed. The holes (channels) were filled with a resin adhesive, and the structure was solidified.

3. Evaluation (1) Photocatalytic Reaction Experiment

Formaldehyde was dispersed in the air to prepare 3.0 L of polluted air having a concentration of 0.5 ppm. The resulting polluted air and the filtering device manufactured as described above were placed in the same apparatus as in the First Embodiment.

The resulting polluted air was circulated at a flow rate of 0.3 L/min, while AC electric fields having the voltages and frequencies shown in Table 2 were applied between the electrodes. The time elapsed until the formaldehyde concentration reached zero was measured.

As a comparative example, photocatalytic particles were molded into a diameter of 100 mm and a thickness of 300 μm by dry pressing, and a porous structure having a porosity of 65% was formed. A photocatalytic reaction experiment was conducted while this photocatalytic sheet was irradiated from above and below by a UV LED lamp having an output of 5 mW. The wavelength of emitted light was 360 nm. The lamp was placed at a distance of 50 mm.

The results are shown in Table 2

TABLE 2

Second Embodiment

| Inner insulating layer thickness (μm) | Light-emitting layer thickness (μm) | Lattice hole size (mm) | Pitch (mm) | Channel surface area ratio (%) | Type of phosphor | Voltage (v) | Frequency (Hz) | Wavelength of emitted light (nm) | Type of photocatalyst | Time for decomposition (min) |
|---|---|---|---|---|---|---|---|---|---|---|
| 30 | 60 | 1 | 1 | 50 | ZnS: Ag, Cl | 120 | 550 | 380 | anatase TiO$_2$ | 18 |
| 30 | 60 | 1 | 1 | 50 | AnS—20MgS: Ag, Cl | 120 | 550 | 366 | anatase TiO$_2$ | 10 |
| 30 | 60 | 1 | 1 | 50 | ZnF$_2$: Gd, Pr, Cu | 120 | 4000 | 311 | anatase TiO$_2$ | 30 |
| * | | | | | | | LED | 360 | anatase TiO$_2$ | 77 |

* Indicates a comparative example

In the filtering device obtained using the surface light-emitting device of the present invention, it was visually confirmed that only the holes emitted light before the photocatalyst was introduced.

The filtering device of the present invention had a shorter decomposition time than when an LED was used. The reason for this is believed to be that light from an external light source is easily reflected by the photocatalytic sheet and cannot efficiently excite the photocatalyst, and also that the light attenuates due to the distance of the light source. In a filtering device obtained using the surface light-emitting device of the present invention, light is concentrated in the holes, the light source is in contact with the filled photocatalyst, and there is little light attenuation because the light source and the photocatalyst are extremely close to each other, whereby the filter is believed to be endowed with high decomposition efficiency.

Thus, the filtering device of the present invention does not need an external light source, and the filter is therefore thin and requires little space.

Third Embodiment

The filtering device was created in the same manner as in the Second Embodiment except that the channels were filled with the photocatalyst, and the following porous layer was overlaid.

(Porous Resin Sheet)

A porous film (porosity 95%) made from a fluorine resin and having a size of 100×100 mm and a thickness of 100 μm was prepared.

Photocatalyst

Anatase TiO$_2$; average grain size: 0.03 μm (commercially available)

A suspension was prepared by dispersing a photocatalyst in ethanol at a concentration of 30 vol %, the porous resin sheet was immersed in this solution, and the sheet was then withdrawn and dried at room temperature. These steps were repeated ten times, and the resulting photocatalyst-supporting sheet was stacked on the top and bottom of the perforated EL sheet.

(Photocatalytic Reaction Experiment)

Figure 8:
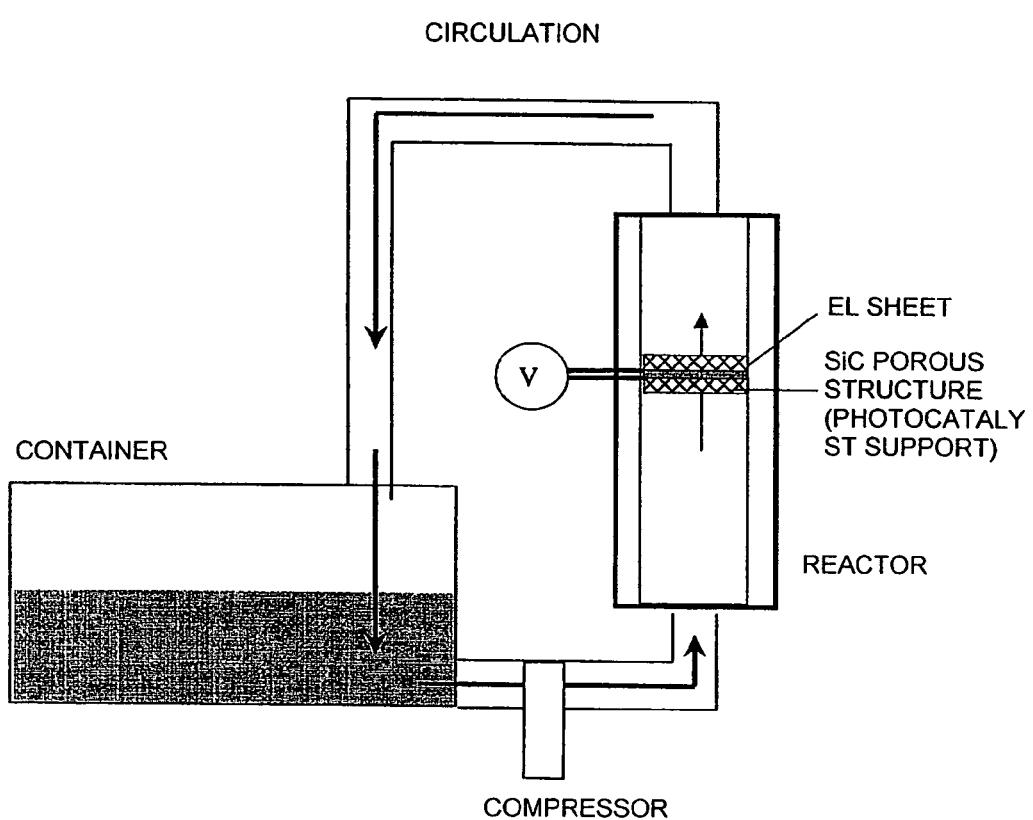
FIG. 8 is an explanatory diagram of a method for evaluating the surface light-emitting device in the embodiments.

Toluene was dispersed in the air to prepare 3.0 L of polluted air having a concentration of 500 ppm. The resulting polluted air and the filtering device manufactured as described above were placed in the same apparatus as shown in FIG. 8.

The resulting polluted air was circulated at a flow rate of 0.3 L/min, while AC electric fields having the voltages and frequencies shown in Table 3 were applied between the electrodes. The time elapsed until the toluene concentration reached zero was measured.

As a comparative example, a photocatalytic reaction experiment was conducted while two stacked sheets supporting the same photocatalyst were irradiated from above and below by a UV LED lamp having an output of 5 mW. The wavelength of emitted light was 360 nm. The lamp was placed at a distance of 50 mm.

The results are shown in Table 3.

TABLE 3

Third Embodiment

| Inner insulating layer thickness (μm) | Light-emitting layer thickness (μm) | Lattice hole size (mm) | Pitch (mm) | Channel surface area ratio (%) | Type of phosphor | Voltage (v) | Frequency (Hz) | Wavelength of emitted light (nm) | Type of photocatalyst | Time for decomposition (min) |
|---|---|---|---|---|---|---|---|---|---|---|
| 30 | 60 | 1 | 1 | 50 | ZnS: Ag, Cl | 120 | 1000 | 380 | anatase TiO$_2$ | 33 |
| 30 | 60 | 1 | 1 | 50 | ZnS—20MgS: Ag, Cl | 120 | 1000 | 366 | anatase TiO$_2$ | 25 |
| 30 | 60 | 1 | 1 | 50 | ZnF$_2$: Gd, Pr, Cu | 120 | 5000 | 311 | anatase TiO$_2$ | 41 |
| * | | | | | | | LED | 360 | anatase TiO$_2$ | 50 |

* Indicates a comparative example

The filtering device of the present invention had a shorter decomposition time than when an LED was used. Even light from an external light source could easily reach the interior of the photocatalytic sheet in cases in which the photocatalytic sheet supporting the photocatalyst had high porosity, as was the case in the present embodiment. Therefore, although the difference in decomposition performance was not as great as in the First Embodiment or the Second Embodiment, the filtering device obtained using the surface light-emitting device of the present invention was confirmed to be superior. The reason for this is believed to be that the photocatalytic sheet is not uniformly irradiated because the light emission of the LED light source is directional.

Thus, the filtering device of the present invention does not need an external light source, and the filter is therefore thin and requires little space.

Fourth Embodiment (1) Ceramic Filter

A multilayered (three-layered) filter, made by NGK Insulators, Ltd., had thirty-seven holes that each had a diameter of 3 mm and was formed in a cross section 30 mm in diameter. The length was 500 mm and the porosity was 35%. This filter successfully separated 100 percent of particles that were 0.2 µm in size. This ceramic filter was cut into lengths of 30 mm to prepare sixteen pieces.

(2) Photocatalytic Coating

The ceramic filter was used to filer a sol (made by Sumitomo Chemical Co., Ltd.) containing a titanium oxide powder responsive to visible light (average grain size 60 nm), or to filter a feed solution containing anatase titanium oxide powder (average grain size 60 nm, made by Tayca Corporation); a titanium oxide layer 10 µm in thickness was formed on the inner walls of the channels; and the layer was baked for one hour at 500° C. under atmospheric conditions and solidified.

(3) Surface Emitter

1. Resin Sheet

A sheet (made by Mitsubishi Rayon Co., Ltd., #000) that transmitted ultraviolet light and had a size of 95×500 mm and a thickness of 100 µm was prepared.

2. Insulating Layer $BaTiO_3$: average grain size: 0.2 µm

Resin: made by Shin-Etsu Chemical Co., Ltd. (trade name: Cyanoresin)

3. Phosphor

ZnS: Cu, Cl powder average grain size: 3 µm

ZnS: Cu, Cl, Al powder average grain size: 3 µm

ZnS-20 mol % MgS: Cu, Cl, Al powder average grain size: 3 µm

ZnS-40 mol % MgS: Cu, Cl, Al powder average grain size: 3 µm

ZnS: Ag, Cl powder average grain size: 3 µm

ZnS-20 mol % MgS: Ag, Cl powder average grain size: 3 µm

In the cases of ZnS: Ag, Cl, and ZnS-20 mol % MgS: Ag, Cl, the phosphor surfaces were coated with $Cu_2S$.

4. Formation of Rear Surface Electrode

A resin sheet was coated with a 0.4-µm Al electrode film by sputtering, and an electrode lead wire was attached to the Al film.

5. Formation of Insulating Layer

A resin was dispersed and dissolved in an amount of 25 vol % relative to cyclohexanone, and a $BaTiO_3$ powder was dispersed (25 vol %) to form a slurry. A coating layer having a thickness of 30 µm was formed by screen printing on the ITO electrode.

6. Formation of Light-Emitting Layer

A resin was dispersed and dissolved in an amount of 25 vol % relative to cyclohexanone. A slurry was formed by subjecting the pulverulent phosphor to a dispersion treatment (25 vol %) in this solution in an Ar gas. A coating layer having a thickness of 60 µm was formed by screen printing on the surface of the insulating layer.

7. Formation of Front Surface Electrode and Sealing

A resin sheet was coated with a 0.2-µm Al electrode film by sputtering, and an electrode lead wire was attached to the Al film.

A light-emitting layer was laid over the Al electrode side of this sheet, and the resulting stack was thermocompression bonded at 120° C. and sealed to form a surface light-emitting sheet.

8. Hole Formation

Seventeen EL sheets manufactured in this manner were prepared by punching the sheets into the same size and structure as the cross section of the ceramic filter in (1).

(4) Assembly

Perforated EL sheets were stacked alternately on the cross section of the 30 mm long ceramic filter, forming a stacked ceramic filter about 480 mm in length.

(5) Filtration Experiment

1. Suspension Preparation 10 mg of aluminum particles with an average grain size of 0.5 µm were dispersed in 10 L of water, trichloroethylene was added, and the solution was adjusted until the concentration reached 1 ppm.

2. Filtration

A filter was placed in a cross-flow filtration apparatus, and an AC electric field of 500 V and 5 kHz was applied between the electrodes of the EL sheet while filtration was performed at a transmembrane pressure difference of 1 $kg/cm^2$. The experiment was also conducted on a ceramic filter with no electric field.

3. Evaluation

The aluminum particle concentration after filtration was measured with an absorptiometer. The trichloroethylene (TCE) concentration after filtration was analyzed with a gas chromatograph.

The results are shown in Table 4.

TABLE 4

Fourth Embodiment

| EL No | Phosphor | Peak wavelength of emitted light (nm) | Voltage (V) | Frequency (Hz) | Brightness (cd/m$^2$) | Photocatalyst | Permeability (L/min) | Aluminum removal ratio (%) | TCE concentration (ppm) |
|---|---|---|---|---|---|---|---|---|---|
| * 1 | none | | 500 | 5000 | | none | 0.4 | 99< | 1.00 |
| 2 | ZnS: Cu, Cl | 516 | 500 | 5000 | 350 | responsive to visible light | 0.22 | 99< | 0.80 |
| 3 | ZnS: Cu, Cl, Al | 455 | 500 | 5000 | 200 | responsive to visible light | 0.22 | 99< | 0.40 |
| 4 | ZnS—20MgS: Cu, Cl, Al | 430 | 500 | 5000 | 122 | responsive to visible light | 0.22 | 99< | 0.53 |
| 5 | ZnS—40MgS: Cu, Cl, Al | 408 | 500 | 5000 | 88 | responsive to visible light | 0.22 | 99< | 0.58 |
| 6 | ZnS: Ag, Cl | 399 | 500 | 5000 | 55 | responsive to visible light | 0.22 | 99< | 0.52 |
| 7 | ZnS—20MgS: Ag, Cl | 369 | 500 | 5000 | 23 | responsive to visible light | 0.22 | 99< | 0.61 |
| 8 | ZnS: Cu, Cl, Al | 455 | 500 | 5000 | 200 | anatase | 0.22 | 99< | 0.81 |
| 9 | ZnS: Ag, Cl | 399 | 500 | 5000 | 55 | anatase | 0.22 | 99< | 0.00 |
| 10 | ZnS—20MgS: Ag, Cl | 369 | 500 | 5000 | 23 | anatase | 0.22 | 99< | 0.00 |

* Indicates a comparative example

As a result of stacking the ceramic filter and the surface emitter and solidifying the photocatalyst on the inner walls of the channels in the ceramic filter, the photocatalyst was provided with a greater surface area than the ceramic filter having a wrapped photocatalytic sheet and surface emitter, and the decomposition efficiency of the TCE was therefore greater.

Fifth Embodiment (1) Ceramic Filter

A multilayered (three-layered) filter, made by NGK Insulators, Ltd., had thirty-seven holes that each had a diameter of 3 mm and was formed in a cross section 30 mm in diameter. The length was 500 mm and the porosity was 35%. This filter successfully separated 100 percent of particles that were 0.2 µm in size.

(2) Photocatalytic Sheet

A polyethylene sheet measuring 95 mm×500 mm and having a porosity of 90% was prepared. This sheet was immersed in a sol (made by Sumitomo Chemical Co., Ltd.) containing a titanium oxide powder responsive to visible light (average grain size 60 nm), or a sol containing anatase titanium oxide powder (average grain size 60 nm, made by Tayca Corporation). The sheet was then taken out and dried at room temperature for 24 hours, and the surface of the resin was coated with a photocatalyst.

(3) Surface Emitter

1. Resin Sheet

A resin sheet (made by Mitsubishi Rayon Co., Ltd., #000) that transmitted ultraviolet light and had a size of 95×500 mm and a thickness of 100 µm was prepared.

2. Insulating Layer

BaTiO$_3$: average grain size: 0.2 µm

Resin: made by Shin-Etsu Chemical Co., Ltd. (trade name: Cyanoresin)

3. Phosphor

ZnS: Cu, Cl powder average grain size: 3 µm

ZnS: Cu, Cl, Al powder average grain size: 3 µm

ZnS-20 mol % MgS: Cu, Cl, Al powder average grain size: 3 µm

ZnS-40 mol % MgS: Cu, Cl, Al powder average grain size: 3 µm

ZnS: Ag, Cl powder average grain size: 3 µm

ZnS-20 mol % MgS: Ag, Cl powder average grain size: 3 µm

In the cases of ZnS: Ag, Cl, and ZnS-20 mol % MgS: Ag, Cl, the phosphor surfaces were coated with Cu$_2$S.

4. Formation of Rear Surface Electrode

A resin sheet was coated with a 0.4-µm Al electrode film by sputtering, and an electrode lead wire was attached to the Al film.

5. Formation of Insulating Layer

A resin was dispersed and dissolved in an amount of 25 vol % relative to cyclohexanone, and a BaTiO$_3$ powder was dispersed (25 vol %) to form a slurry. A coating layer having a thickness of 30 µm was formed by screen printing on the ITO electrode.

6. Formation of Light-Emitting Layer

A resin was dispersed and dissolved in an amount of 25 vol % relative to cyclohexanone. A slurry was formed by subjecting the pulverulent phosphor to a dispersion treatment (25 vol %) in this solution in an Ar gas. A coating layer having a thickness of 60 µm was formed by screen printing on the surface of the insulating layer.

7. Formation of Front Surface Electrode and Sealing

A resin sheet was coated with a 0.2-µm Al electrode film by sputtering, and an electrode lead wire was attached to the Al film.

A light-emitting layer was laid over the ITO electrode side of this sheet, and the resulting stack was thermocompression bonded at 120° C. and sealed to form a surface light-emitting sheet.

8. Hole Formation

Holes measuring 3 mm in diameter were formed at a pitch of 3 mm in the surface of this sheet using a punching machine. The cross section of these holes was then sealed with an adhesive.

(4) Assembly

A photocatalytic sheet was wrapped around the side surface of the ceramic filter, and a surface emitter was wrapped over the photocatalytic sheet.

(5) Filtration Experiment

1. Suspension Preparation 10 mg of aluminum particles with an average grain size of 0.5 μm were dispersed in 10 L of water, trichloroethylene was added, and the solution was adjusted until the concentration reached 1 ppm.

2. Filtration

A filter was placed in a cross-flow filtration apparatus, and an AC electric field of 500 V and 5 kHz was applied between the electrodes of the EL sheet while filtration was performed at a transmembrane pressure difference of 1 kg/cm$^2$. The experiment was also conducted on a ceramic filter with no electric field.

3. Evaluation

The aluminum particle concentration after filtration was measured with an absorptiometer. The trichloroethylene (TCE) concentration after filtration was analyzed with a gas chromatograph.

The results are shown in Table 5.

greater. Decomposition performance was not as high when a photocatalyst responsive to visible light was combined with an EL sheet that emitted ultraviolet light having a peak wavelength of 400 nm or less. The reason for this is believed to be that the light emitted by the EL sheet had lower intensity (the sum of the intensity of visible light and the intensity of ultraviolet light).

High decomposition performance was exhibited with a UV-emitting EL sheet in cases in which an anatase photocatalyst was used. The reason for this is believed to be that the anatase photocatalyst performance was greater than that of a photocatalyst responsive to visible light, and relatively high photocatalytic performance was therefore achieved even when the intensity of the light emitted by the EL sheet (the sum of the intensity of visible light and the intensity of ultraviolet light) was low.

INDUSTRIAL APPLICABILITY

The surface light-emitting device of the present invention can be used as a filtering device. In this case, substances that are larger than the pores in a porous structure having a catalytic function are collected from among particles suspended in a fluid. Since the surface light-emitting device of the present invention can be made to have an extremely thin structure, the device has various applications and yields significant effects when used as a filter for air purification or the like. For example, an air conditioner or the like can be provided with an air purifying function when the device is placed in the air intake opening of the air conditioner.

TABLE 5

Fifth Embodiment

| EL No | EL sheet Phosphor | Peak wavelength of emitted light (nm) | Voltage (V) | Frequency (Hz) | Brightness (cd/m$^2$) | Photocatalyst | Permeability (L/min) | Aluminum removal ratio (%) | TCE concentration (ppm) |
|---|---|---|---|---|---|---|---|---|---|
| * 1 | none | | | | | none | 0.40 | 99< | 1.00 |
| 2 | ZnS: Cu, Cl | 516 | 500 | 5000 | 350 | responsive to visible light | 0.38 | 99< | 0.90 |
| 3 | ZnS: Cu, Cl, Al | 455 | 500 | 5000 | 200 | responsive to visible light | 0.38 | 99< | 0.50 |
| 4 | ZnS—20MgS: Cu, Cl, Al | 430 | 500 | 5000 | 122 | responsive to visible light | 0.38 | 99< | 0.62 |
| 5 | ZnS—40MgS: Cu, Cl, Al | 408 | 500 | 5000 | 88 | responsive to visible light | 0.38 | 99< | 0.65 |
| 6 | ZnS: Ag, Cl | 399 | 500 | 5000 | 55 | responsive to visible light | 0.38 | 99< | 0.60 |
| 7 | ZnS—20MgS: Ag, Cl | 369 | 500 | 5000 | 23 | responsive to visible light | 0.38 | 99< | 0.70 |
| 8 | ZnS: Cu, Cl | 516 | 500 | 5000 | 350 | anatase | 0.38 | 99< | 0.98 |
| 9 | ZnS: Cu, Cl, Al | 455 | 500 | 5000 | 200 | anatase | 0.38 | 99< | 0.90 |
| 10 | ZnS: Ag, Cl | 399 | 500 | 5000 | 55 | anatase | 0.38 | 99< | 0.20 |
| 11 | ZnS—20MgS: Ag, Cl | 369 | 500 | 5000 | 23 | anatase | 0.38 | 99< | 0.00 |

* Indicates a comparative example

As a result of wrapping the photocatalytic sheet and the surface emitter, not only was a filtration function achieved, but TCE could also be decomposed. When a photocatalyst responsive to visible light was used, decomposition progressed as the wavelength of emitted light grew shorter. The reason for this is believed to be that the energy of the light was The surface light-emitting device of the present invention is characterized in having an efficient heat radiation function because of the presence of through-holes, for which reason the surface emitter does not easily deteriorate from heat even when high voltages and high frequencies are applied to emit light.

The surface light-emitting device of the present invention can be used in display applications while transmitting air or other gases. The display would have a long service life because heat generation can be prevented in this case as well.

The surface light-emitting device of the present invention can be applied to various fields, including the decomposition and removal of contaminants in the atmosphere, such as NOx, SOx, CO gas, diesel particulates, pollen, dust, and ticks; the decomposition and removal of organic compounds contained in sewage; the sterilization of common bacteria and viruses; the decomposition of harmful gases produced by chemical plants; the decomposition of odorous components; and the like. As a manufactured product, the present invention can be developed as all kinds of filters in the aforementioned fields, and can be applied to air purification, sewage filtration, various types of water purifiers, insect repellent, and the like.

The present invention can also be used in EL displays, light sources for backlights in portable phones, light sources for fixing toner used in digital photo printers for digital cameras, light sources for curing UV cured resins, and sterilizing light sources in medical photocatalyst-coated catheters.

When combined with an afterglow phosphor that emits visible light, the present invention can be used as a display or filter that emits light by means of AC electric fields during daylight hours, and continues to emit light without a power source during nighttime hours.

The present invention can also be used as a sheet-like insect-attracting panel by taking advantage of the fact that insects are drawn to ultraviolet light having an average wavelength of 365 nm. This application is effective for preventing malaria or the like.

The optically assisted ceramic filter of the present invention is a ceramic filter that can excite a photocatalyst with a surface emitter for emitting visible light or ultraviolet light, and that has a function for decomposing organic matter or destroying bacteria or viruses. The filter can be placed and operated in a low-clarity liquid, whereby a catalytic reaction can be efficiently performed without the use of an ultraviolet lamp, an ultraviolet LED, or another such external ultraviolet light source. Particularly, a catalytic reaction can be efficiently performed even in the case of a highly UV-absorbing low-clarity fluid that cannot be treated with an external light source.

The optically assisted ceramic filter of the present invention is generally used to filter liquids, but can also function as a filter for gases. For example, in cases in which NOx, SOx, and other such harmful gases are contained in the atmosphere together with soot dust and diesel particulates, the soot dust and diesel particulates can be collected by the filtering function, and the NOx and other gases can be decomposed by the photocatalytic function. The present invention can also be applied to various fields, including the decomposition and removal of pollen, dust, and ticks; the decomposition and removal of organic compounds contained in sewage; the sterilization of common bacteria and viruses; the decomposition of harmful gases produced by chemical plants; and the decomposition of odorous components. As a manufactured product, the present invention can be developed as all kinds of filters in the aforementioned fields, and can be applied to air purification, sewage filtration, various types of water purifiers, insect repellent, and the like.

The invention claimed is:

1. A surface light-emitting device comprising:
   a surface emitter for emitting visible light or ultraviolet light by electroluminescence; and
   a plurality of through-holes defining channels for fluid flow in a direction orthogonal to the surface of the surface emitter, characterized in that the surface emitter has light-emitting layers placed in a lattice formation, the gaps constituting the channels.

2. The surface light-emitting device according to claim 1, wherein
   the surface emitter includes a porous layer having a photocatalyst that is disposed on the top and/or bottom surfaces of the surface emitter.

3. The surface light-emitting device according to claim 2, characterized in that the porous layers having a photocatalyst are a foamed metal, a foamed ceramic, or a woven resin fabric.

4. The surface light-emitting device according to claim 2, wherein the porous layers having a photocatalyst are ceramic filters.

5. The surface light-emitting device according to claim 4, characterized in that
   the ceramic filters have a plurality of channels; and
   the channels are communicated with the channels of the surface light-emitting device.

6. The surface light-emitting device according to claim 2, characterized in that the porous layers and porous structure having a photocatalyst have an average pore diameter of no greater than 500 μm.

7. The surface light-emitting device according to claim 2, characterized in that the surface emitter and the porous layers are repeatedly stacked.

8. The surface light-emitting device according to claim 1, characterized in that the channels are filled with a porous structure having a photocatalyst.

9. The surface light-emitting device according to claim 1, characterized in that except for electrode portions, the surface emitter is electrically insulated from an exterior of the surface light-emitting device.

10. The surface light-emitting device according to claim 1, characterized in that the surface emitter has a plurality of rectangular light-emitting layers placed at fixed gap intervals, wherein the gaps constitute the channels.

11. The surface light-emitting device according to claim 1, wherein the emitted visible light or ultraviolet light is concentrated in the channels.

12. The surface light-emitting device according to claim 1, characterized in that the surface area occupied by the channels is 30 to 70% of the entire surface of the surface emitter.

13. The surface light-emitting device according to claim 1, characterized in that the peak wavelength of the spectrum of light emitted by the surface emitter is 540 nm or less.

14. The surface light-emitting device according to claim 13, characterized in that the peak wavelength of the spectrum of light emitted by the surface emitter is 460 nm or less.

15. The surface light-emitting device according to claim 14, characterized in that the peak wavelength of the spectrum of light emitted by the surface emitter is 400 nm or less.

16. The surface light-emitting device according to claim 1, characterized in that an inorganic EL device or an organic EL device is used as the surface emitter.

17. A surface light-emitting device comprising:
   a surface emitter for emitting visible light or ultraviolet light by electroluminescence; and
   a plurality of through-holes defining channels for fluid flow in a direction orthogonal to the surface of the surface emitter, wherein the emitted light is concentrated in the channels, and the light-emitting layers of the surface emitter are enclosed by members that reflect visible light and/or ultraviolet light.

18. A surface light-emitting device comprising:
a surface emitter for emitting visible light or ultraviolet light by electroluminescence, the surface emitter being an inorganic EL device or an organic EL device; and
a plurality of through-holes defining channels for fluid flow in a direction orthogonal to the surface of the surface emitter,
the general formula for the phosphor used in the inorganic EL device is $Zn_{(1-x)}A_xS$: Cu, D, wherein A is at least one type of 2A group element selected from among Be, Mg, Ca, Sr, and Ba; D is at least one type of element selected from among 3B group elements or 7B group elements; and the value of x is $0 \leq x \leq 1$; and
the phosphor has a function for emitting Blue-Cu light.

19. A surface light-emitting device comprising:
a surface emitter for emitting visible light or ultraviolet light by electroluminescence, the surface emitter being an inorganic EL device or an organic EL device; and
a plurality of through-holes defining channels for fluid flow in a direction orthogonal to the surface of the surface emitter, wherein,
the general formula for the phosphor used in the inorganic EL device is $Zn_{(1-x)}A_xS$: Ag, D wherein A is at least one type of 2A group element selected from among Be, Mg, Ca, Sr, and Ba; D is at least one type of element selected from among 3B group elements or 7B group elements; and the value of x is $0 \leq x \leq 1$; and
the phosphor has a function for emitting Blue-Cu light.

20. A filtering device comprising the surface light-emitting device according to claim 1.

21. A filter for an air purifier or an air conditioner comprising the filtering device according to claim 20.

22. An optically assisted ceramic filter, comprising:
a ceramic filter having a plurality of channels; and
a photocatalytic layer and a surface emitter disposed on a side surface of the ceramic filter, the surface emitter being configured to emit light by dispersive inorganic EL with the inorganic EL electrodes being formed from a light-reflecting material.

23. The optically assisted ceramic filter according to claim 22, characterized in that the channels of the ceramic filter are orthogonal to a cross section of the ceramic filter.

24. The optically assisted ceramic filter according to claim 22, characterized in that a plurality of through-holes are formed in the surface emitter in a direction orthogonal to the surface of the surface emitter.

25. The optically assisted ceramic filter according to claim 22, characterized in that the peak wavelength of the spectrum of light emitted by the surface emitter is 460 nm or less.

26. The optically assisted ceramic filter according to claim 25, characterized in that the peak wavelength of the spectrum of light emitted by the surface emitter is 400 nm or less.

27. An optically assisted ceramic filter according to comprising:
a ceramic filter having a plurality of channels; and
a photocatalytic layer and a surface emitter disposed on a side surface of the ceramic filter, the surface emitter emitting light by dispersive inorganic EL, and wherein
the general formula for the phosphor used in the inorganic EL device is $Zn_{(1-x)}A_xS$: Cu, D wherein A is at least one type of 2A group element selected from among Be, Mg, Ca, Sr, and Ba; D is at least one type of element selected from among 3B group elements or 7B group elements; and the value of x is $0 \leq x \leq 1$; and
the phosphor has a function for emitting Blue-Cu light.

28. An optically assisted ceramic filter comprising:
a ceramic filter having a plurality of channels; and
a photocatalytic layer and a surface emitter disposed on a side surface of the ceramic filter, the surface emitter emitting light by dispersive inorganic EL, and wherein
the general formula for the phosphor used in the inorganic EL device is $Zn_{(1-x)}A_xS$: Ag, D wherein A is at least one type of 2A group element selected from among Be, Mg, Ca, Sr, and Ba; D is at least one type of element selected from among 3B group elements or 7B group elements; and the value of x is $0 \leq x \leq 1$; and
the phosphor has a function for emitting Blue-Cu light.

* * * * *

UNITED STATES PATENT AND TRADEMARK OFFICE
CERTIFICATE OF CORRECTION

PATENT NO. : 7,767,158 B2
APPLICATION NO. : 11/628947
DATED : August 3, 2010
INVENTOR(S) : Chihiro Kawai It is certified that error appears in the above-identified patent and that said Letters Patent is hereby corrected as shown below:

Col. 29, line 13, change "$0 \leqq x \leqq 1$" to --$0 < x < 1$--.

Col. 29, line 13, change "$0 \leqq x \leqq 1$" to --$0 < x < 1$--.

Col. 30, line 14, delete "according to"; and in line 12, change "$0 \leqq x \leqq 1$" to --$0 < x < 1$--.

Col. 30, line 25, change "$0 \leqq x \leqq 1$" to --$0 < x < 1$--.

Signed and Sealed this

Ninth Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,767,158 B2                                         Page 1 of 1
APPLICATION NO.   : 11/628947
DATED             : August 3, 2010
INVENTOR(S)       : Chihiro Kawai It is certified that error appears in the above-identified patent and that said Letters Patent is hereby corrected as shown below:

Column 29, line 13 (claim 18, line 13) change "$0 \leqq x \leqq 1$" to --$0 < x < 1$--.

Column 29, line 27 (claim 19, line 13) change "$0 \leqq x \leqq 1$" to --$0 < x < 1$--.

Column 30, line 14 (claim 27, line 1) delete "according to"; and in Column 30, line 25 (Claim 27, line 12) change "$0 \leqq x \leqq 1$" to --$0 < x < 1$--.

Column 30, line 37 (claim 28, line 11) change "$0 \leqq x \leqq 1$" to --$0 < x < 1$--.

This certificate supersedes the Certificate of Correction issued November 9, 2010.

Signed and Sealed this
Twenty-fifth Day of January, 2011

David J. Kappos
*Director of the United States Patent and Trademark Office*